US005939534A

United States Patent [19]
Inoue et al.

[11] Patent Number: 5,939,534
[45] Date of Patent: Aug. 17, 1999

[54] FACTORS MUTATED IN THE D1 CAP REGION

[75] Inventors: Makoto Inoue, Toyonaka; Kaoru Kikuchi, Takarazuka; Yoko Ishige, Toyonaka; Akira Ito, Takarazuka; Toru Kimura, Kusatsu; Chikao Nakayama, Sanda; Hiroshi Noguchi, Kawanishi, all of Japan

[73] Assignee: Sumitomo Pharmaceuticals Company, Limited, Osaka, Japan

[21] Appl. No.: 08/669,284

[22] PCT Filed: Dec. 27, 1994

[86] PCT No.: PCT/JP94/02269

§ 371 Date: Jun. 28, 1996

§ 102(e) Date: Jun. 28, 1996

[87] PCT Pub. No.: WO95/18150

PCT Pub. Date: Jul. 6, 1995

[30] Foreign Application Priority Data

Dec. 29, 1993 [JP] Japan .................................. 5-350934
Aug. 2, 1994 [JP] Japan .................................. 6-201504
Oct. 5, 1994 [JP] Japan .................................. 6-268281

[51] Int. Cl.$^6$ ........................ C12N 15/18; C07K 14/475; C07K 14/535; C07K 14/52
[52] U.S. Cl. ........................... 530/399; 530/350; 530/351
[58] Field of Search ....................... 530/350, 351, 530/399; 435/69.1, 320.1, 325; 536/23.51

[56] References Cited

U.S. PATENT DOCUMENTS 5,349,056  9/1994  Panayotatos .

OTHER PUBLICATIONS

Robinson, R.C. et al., *Cell*, 77(7): 1101–1116, 1994.

Bazan, J.F. et al., *Neuron*, 7(2): 197–208, 1991.

Brakenhoff, J.P.J. et al., *J. Biol. Chem.*, 269 (1): 86–93, 1994.

Sprang, S.R. et al., *Curr. Opin. Struct. Biol.*, 3(6): 815–27, 1993.

Panayotatos, N. et al., *J. Biol. Chem.*, 268(25): 19000–19003, 1993.

Boulay, J.L. et al., *Current Biology*, 3(9): 573–81, 1993.

*Primary Examiner*—Marianne P. Allen
*Attorney, Agent, or Firm*—Sughrue, Mion, Zinn, Macpeak & Seas, PLLC

[57] ABSTRACT

Human ciliary neurotrophic factor (human CNTF) mutants, in which at least the amino acid residue corresponding to position 153 of wild type human CNTF has been substituted with another amino acid residue in the amino acid sequence encoding human CNTF, exhibit an activity comparable or superior to that of wild type human CNTF. It is therefore expected that the human CNTF mutants would be effective as drugs with improved side effects such as reduction in appearance of an autoantibody, loss of body weight, anorexia, a dry cough, fatigue, etc.

In cytokines having sequence similarity to human CNTF and abundant α helices (GH, PRL, EPO, G- CSF, LIF, IL-6, IL-2, IL-4, GM-CSF), there are further provided mutants in the D1 cap region.

8 Claims, 20 Drawing Sheets

REACTION SOLUTION
FOR PCR (FIRST)

| | |
|---|---|
| pKKCNTF | 500ng |
| PRIMER 1(#N OR #C) | 100pmol |
| PRIMER 2(EACH MUTATION SITE) | 100pmol |
| dNTP | 0.25mM |
| x10 BUFFER | 10 μL |
| pfu POLYMERASE | 2.5U |
| H₂O | TOTAL 100 μL |

REACTION CYCLE

94°C  5 MIN.
  ↓
94°C  1 MIN. ⎤ 30
50°C  1 MIN. ⎥ 2
75°C  3 MIN. ⎦ 50 CYCLE
  ↓
75°C  8 MIN.

FIG.4A

REACTION SOLUTION
FOR PCR (SECOND)

| | |
|---|---|
| pKKCNTF (LINEAR) | 200ng |
| PRIMER 1(PRODUCT FROM THE FIRST PCR) | CA. 2pmol |
| PRIMER 1(#N OR #C) | 50pmol |
| dNTP | 0.25mM |
| x10 BUFFER | 10 μL |
| pfu POLYMERASE | 2.5U |
| H₂O | TOTAL 100 μL |

REACTION CYCLE

94°C  5 MIN.
  ↓
94°C  1 MIN. ⎤
60°C  1 MIN. ⎥ 50 CYCLE
75°C  3 MIN. ⎦
  ↓
75°C  8 MIN.

FIG.4B

REACTION SOLUTION
FOR PCR (THIRD)

| | |
|---|---|
| TEMPLATE (PRODUCT FROM THE SECOND PCR) | Q.A. |
| PRIMER 1#N | 25pmol |
| PRIMER 2#C | 50pmol |
| dNTP | 0.25mM |
| x10 BUFFER | 5 μL |
| pfu POLYMERASE | 1.25U |
| H₂O | TOTAL 50 μL |

REACTION CYCLE

94°C  5 MIN.
  ↓
94°C  1 MIN. ⎤
50°C  1 MIN. ⎥ 30 CYCLE
75°C  3 MIN. ⎦
  ↓
75°C  8 MIN.

| | | |
|---|---|---|
| #N | : 5'-CGG<u>AGATCT</u>TTTTTTATAAAATCAGGAGG-3' | (29mer) |
| | !      !(BglII) | |
| #C(RV) | : 5'-CAAGCTTGGATGCATGTCAGAGAAGGGAC-3' | (29mer) |
| |   (3'-GTTCGAACC<u>TACGTA</u>CAGTCTCTTCCCTG-5') | |
| |            !      !(EcoT22I) | |
| pF152 | : 5'-GTGGTCTC···*GAGAAGAAGCTG-3' | (23mer) |
| pE153 | : 5'-GGTCTCTTT···*AAGAAGCTGTG-3' | (23mer) |
| pK154 | : 5'-CTCTTTGAG···*AAGCTGTG-3' | (21mer) |
| pK155 | : 5'-CTTTGAGAAG···*CTGTGGG-3' | (21mer) |
| pL156 | : 5'-GAGAAGAAG···*TGGGGCCTAAAG-3' | (24mer) |
| pW157 | : 5'-GAAGAAGCTG···*GGCCTAAAG-3' | (22mer) |
| pQ63R | : 5'-GCTCACTCCAACGATCAGTGC-3' | (21mer) |

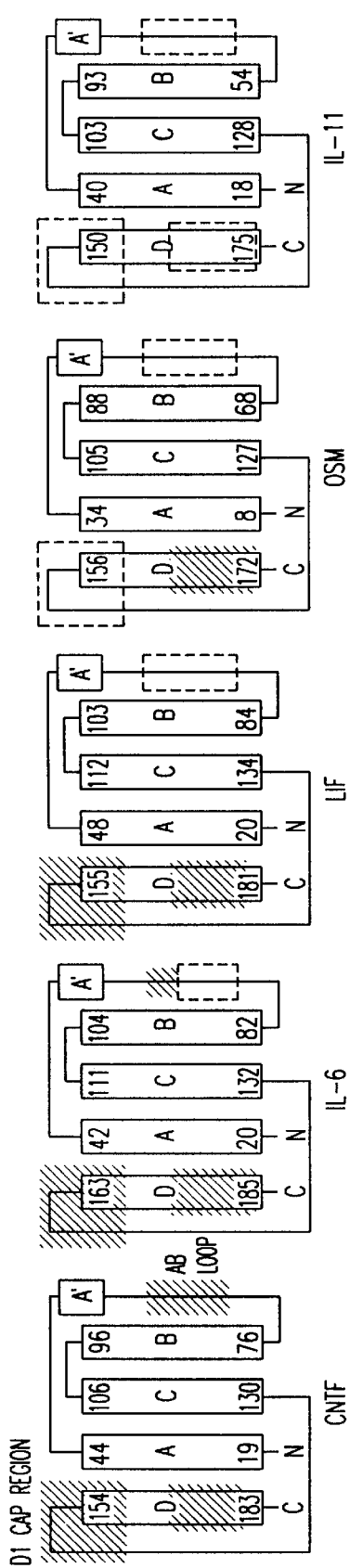
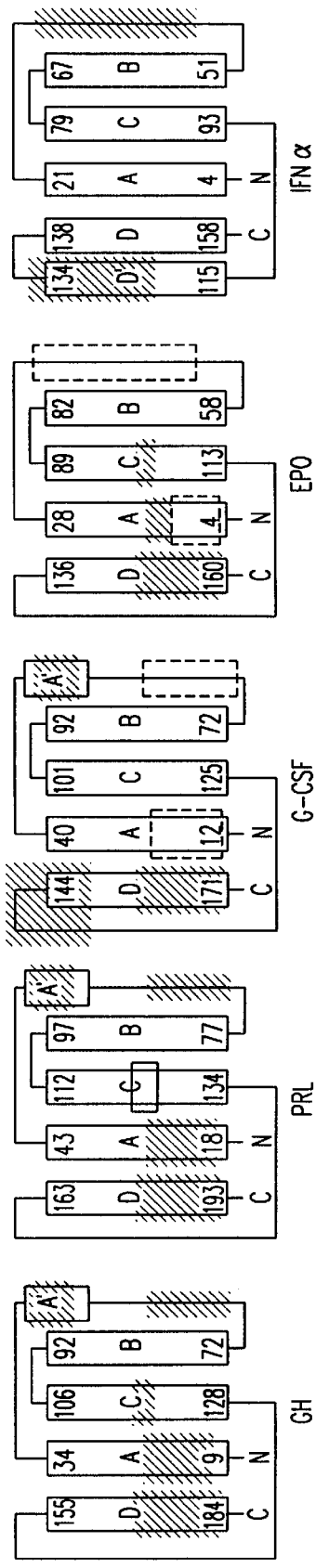

FACTORS MUTATED IN THE D1 CAP REGION

TECHNICAL FIELD

The present invention relates to a novel mutant of a human ciliary neurotrophic factor (hereinbelow abbreviated as human CNTF) and a protein having a four-helix bundle structure similar to that of human CNTF, which are expected to be useful for the treatment of neuropathic diseases. The present invention also relates to a DNA containing the nucleotide sequence encoding the mutant and an expression vector carrying the DNA as well as a transformant transformed with the expression vector.

BACKGROUND ART

Human CNTF was discovered by Silvio Varon et al. in 1979 to be a factor for promoting the survival of ciliary ganglions which are parasympathetic nerves (Brain Res., 173, 29–45 (1979)). Subsequently, the purification and cloning of human CNTF were reported in G. Barbin et al., J. Neurochem., 43, 1468–1478 (1984); L. F. Lin et al., Science, 246, 1023 (1989); P. Masiakowski et al., J. Neurochem., 57, 1003 (1991); A. Negro et al., Dur. J. Biochem, 201, 289 (1991); J. R. McDonald et al., Biochim. Biophys. Acta, 70, 1090 (1991); WO 90/7341 and WO 91/4316.

In connection with the pharmacological activities of human CNTF in vitro, there are the following reports on the survival promoting activity of human CNTF on hippocampal and septal GABA-mediated neurons (N. Y. IP et al., N. Neursci., 11, 3124–3134 (1991)); on optic neurons (H. D. Hoffman, J. Neurochem., 51, 109–113 (1988)); on sensory neurons (G. Barbin et al., J. Neurochem., 43, 1468–1478 (1984)); on parasympathetic neurons (Y. Arakawa et al., J. Neursci., 10, 3507–3515 (1990)) and on motor neurons (M. Sendtner et al. J. Cell Sciences supple., 15, 103–109 (1991)); and on the differentiation activity of human CNTF into cholinergic neurons (S. Saadat et al., J. Cell Biol., 108, 1807–1816 (1989) and U. Ernsberger et al., Neuron, 2, 1275–1284 (1989)) and into type 2A astrocytes (D. J. Anderson et al., TINS, 12, 83 (1989)); the in vivo activities are reported on the survival promoting effect on septal cholinergic neurons in a fimbria-fornix trunsection model (T. Hagg et al., Neuron, 8, 145 (1992))1D on the survival promoting activity of human CNTF on motor neurons in an axotomy model (M. Sendtner et al., Nature, 345, 440–441 (1990)); on the survival promoting activity of human CNTF on motor neurons in mice with genetic motor disorders (M. Sendtner et al. in Nature, 358, 502–503 (1992)); on the protecting effect of human CNTF for substantia nigra dopaminergic neurons in a substantia nigra-striatun trunsection model (T. Hogg & S. Varon, Proc. Natl. Acad. Sci., USA, 90, 6315–6319 (1993)); on the protecting effect for a photoreceptor (M. M. LaVail et al., Proc. Natl. Acad. Sci., USA, 89, 11249–11253 (1992)); on the protecting effect for optic neurons (K. Unoki & M. M. LaVail in Investigative Ophthalmology & Visual Sciences 35, 907–915 (1994)); and so on.

As reported above human CNTF acts on neurons to exert the activities of promoting the survival of neurons, accelerating the neurite outgrowth of neurons and stimulating the synthesis of neurotransmitters. Human CNTF is thus expected to be useful for the treatment of trauma-induced nervous disorders, diseases caused by atrophy or denaturation of neurons including Alzheimer's disease, cerebrovascular dementia and amyotrophic lateral sclerosis (J. E. Springer, DN & P, 4, 394 (1991) R. M. Lindsay, Neurobiol. of Aging, 15, 249–251 (1994) and R. M. Lindsay, TINS, 17, 182 (1994)).

It is also reported that human CNTF effectively displays, in combination with brain-derived neurotrophic factor (BDNF) a protecting activity on nervous disorders in a neurodegenerative animal model (Wobbler mice) (H. Mitsumoto et al., Science, 265, 1107–1110 (1994)). It is suggested that human CNTF will be an effective drug for the treatment of nervous disorders, not only by human CNTF alone but also in combination with other neurotrophic factors (R. Nishi, Sciences, 265, 1052–1053 (1994)).

However, in clinical trials of wild type human CNTF currently used in USA for the treatment of amyotrophic lateral sclerosis, a considerably large doses e.g., 6 mg/week, of human CNTF is administered (Bio World Today, Sep. 8, 1993). Generally, in consecutive administration of a proteinaceous preparations an increased dose tends to involve such problems that side effects might be caused due to the generation of an autoantibody and that the production costs might increase. In fact, the formation of antibodies is observed during the CNTF evaluation in phase II and phase III in USA (BIO World Todays Sep. 8, 1993). Furthermore, an additional problem arises to cause other side effects (BIO World Todays Jun. 24, 1994 and Science, 264., 772–774 (1994)). It is therefore expected that the foregoing problems caused by the use of wild type human CNTF will be improved, if a mutant of human CNTF having a higher specific activity than that of the wild type is employed.

It is reported that human CNTF is composed of 200 amino acid residues, abundant in $\alpha$-helix and contains 53% $\alpha$-helix and 9% $\beta$-turn structure (A. Negro et al., J. Neurosci. Res., 29, 251 (1991)). Analysis of the secondary structure suggests that human CNTF would take a structure similar to that of $\alpha$-helical cytokines. It is reported that human CNTF has a 4-helix bundle structure which is commonly observed in all $\alpha$-helical cytokines, such as growth hormone (hereinafter abbreviated as GH), prolactin (hereinafter abbreviated as PRL), erythropoietin (hereinafter abbreviated as EPO), granulocyte colony-stimulating factor (hereinafter abbreviated as G-CSF) oncostatin H (OSM), leukemia inhibitory factor (hereinafter abbreviated as LIF) and some interleukins (J. F. Bazan, Neuron, 7, 197 (1991)). The four helices are designated successively as A, B, C and D from the N terminus.

Proteins having a 4-helix bundle structure are classified into a long-chain group comprising 160 to 200 amino acid residues in length and a short-chain group comprising 105 to 145 amino acid residues in length (J. L. Boulay & W. E. Paul, Curr. Biol., 3, 573 (1993) and S. Sprang & J. Bazan, Curr. Opin. Struct. Biol., 3, 815 (1993)). The long-chain group includes GH, PRL, EPO, G-CSF, LIF, interleukin 6 (hereinafter abbreviated as IL-6) and the like; the short-chain group includes interleukin 2 (hereinafter abbreviated as IL-2), interleukin 4 (hereinafter abbreviated as IL-4) and granulocyte macrophage colony-stimulating factor (hereinafter abbreviated as GM-CSF) and the like. Human CNTF is one of the long-chain group proteins and predicted to be more closely akin to the proteins of this group.

With respect to the proteins mentioned above, many results on the structure-activity relationship have been reported to date. These reports point out that the amino acid residues between helices A and B (hereinafter referred to as AB loop region) and helix D region are important for expressing the biological activity of many $\alpha$-helical cytokines. Similar reports are also seen on IL-6 (R. Savino et al., Proc. Natl. Acad. Sci. USA, 90, 4067 (1993) C. Lutticken et al., FEBS Lett. 282, 265 (1991), J. P. J. Brakenhoff et al., J. Immunol., 145, 561 (1990) and X. Li et al., J. B. C, 268, 22377 (1993)). Regarding GH, a similar importance is observed with GH mutant constructed (B. C. Cunningham et al., Science, 247, 1461 (1990)) and the structure of the GH mutant has been directly determined by crystallography of the complex of GH and a GH receptor (A. M. DeVos et al., Science, 255, 306 (1992)).

On the other hand, Bazan reported that there is a similarity of amino acid sequence, which is called D1 motif, in the boundary region (hereinafter referred to as D1 cap region) between the amino acid residues which link helix C and helix D (hereinafter referred to as CD loop region) and helix D (J. F. Bazan, Neuron, 7 197 (1991)). The amino acid sequence of D1 motif is represented by:

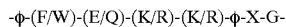

wherein φ is a hydrophobic residue and X is any residue. The D1 motif corresponds to the amino acid residues 151–158 in human CNTF. This region is considered as corresponding to the respective amino acids of, e g., LIF (amino acid residues 154–161) OSM (amino acid residues 159–166) IL-6 (amino acid residues 157–164) and IL-11 (amino acid residues 148–155). The boundary region of CD loop and helix D was reported to be important for receptor binding of IL-6 (J. P. J. Brakenhoff et al., J. B. C., 269, 86 (1994)) and LIF (R. C. Robinson et al., Cell, 77, 1101 (1994)). However, the amino acid sequence in the D1 cap region of IL-6 lacks similarity with the D1 motif and hence it has not been identified what amino acids on the D1 motif are important. In the same regions LIF has great similarity in the amino acid sequence to the D1 motif but what amino acid residues are important has not been identified. There is no other report on other α-helical cytokines to suggest that the foregoing region would be important for their biological activity.

In human CNTF, three receptors, i.e., CNTF receptor α (hereinafter abbreviated as CNTF-Rα), LIF receptor (hereinafter abbreviated as LIF-R) and gp130 are responsible for the signal transduction into cells. gP130 is a constituent of the receptor not only for human CNTF but for IL-6, LIF, OSM and interleukin 11 (hereinafter abbreviated as IL-11) in common (S. Davis et al., Science, 253, 59 (1991), S. Davis et al, ibid., 260, 1805 (1993), D. P. Gearing et al., ibid., 255, 1434 (1992) and N. Y. Ip et al., Cell, 69, 1121 (1992)). In view of the aforesaid structural similarity and also the same receptor being commonly involved, it is highly likely that in human CNTF, IL-6, LIF, OSM and IL-11 the amino acid residue corresponding to the same region in each ligand will be associated with receptor binding Other α-helical cytokines which have structural similarity to CNTF have also been studied for clinical application to develop for the treatment of various diseases With respect to many cytokines including GM-CSF, macrophage colony stimulating factor (hereinafter abbreviated as H-CSF), interleukin 3 (hereinafter abbreviated as IL-3) and IL-6, clinical tests have been performed or are under consideration, as described in ZOKETSU INSHI (Hematopoietic Factor), 5, 6–86 (1994).

There is a possibility that, even in the case of other α-helical cytokines, the use of mutant proteins having higher activities than wild type proteins may effectively improve the problems similar to those of wild type CNTF.

DISCLOSURE OF INVENTION

The present inventors have found that the substitution of the amino acid residue, at least at position 153, in the amino acid sequence of wild type human CNTF can effectively enhance the CNTF activity, and have created a novel mutant protein of human CNTF having a specific activity comparative or superior to that of naturally occurring human CNTF by substituting glutamic acid residue at position 153 with another amino acid residue. The inventors have further found that by substituting, in addition to the substitution of the amino acid residue at position 153, the amino acid residue at position 63 in naturally occurring human CNTF with another amino acid residue such as arginine residue, the specific activity can be increased to the sum of the respective activities achieved by the double substitutions at positions 153 and 63.

The inventors have also found that 155 lysine residue is essential and indispensable for the human CNTF activity during the course of clarifying the role of the D1 cap region through the amino acid substitution technique. These findings reveal that the substitution of the 153 amino acid is effective for enhancing the CNTF activity as described above. And the respective roles of the other amino acid residues of D1 cap region have also been clarified. In addition to the importance of the D1 cap region in human CNTF which has been clarified, detailed comparison in amino acid sequence suggests that the region corresponding to the D1 cap region will be associated with expression of the activity also in α-helical cytokines other than CNTF which have structural similarity to CNTF. That is, it is highly predictable that by mutating the D1 cap region, especially by mutating the amino acid residue corresponding to the 153 amino acid of human CNTF, a mutant protein having a high specific activity as compared to that of native protein will be obtained. The 153 glutamic acid residue in human CNTF corresponds to, for example, 156 glutamine residue in LIF and 161 glutamine residue in OSM.

That is, the present invention relates to:

(1) A mutant protein of a protein having a 4-helix bundle structure wherein the helices are designated successively as AD By C and D from the N terminus and containing a region designated as a D1 cap region, which is the boundary region between helix D and CD loop region which links helix C and helix D, and has an amino acid sequence represented by:

wherein φ is a hydrophobic residue and X is any residue;
at least one amino acid residue in the amino acid sequence corresponding to said D1 cap region being substituted with another amino acid residue.

(2) A mutant protein according to (1), wherein said protein having a 4-helix bundle structure is a protein utilizing gp130 as a receptor for transducing a signal into a cell.

(3) A mutant protein according to (1), wherein the protein having a 4-helix bundle structure is a protein utilizing gp130 as a receptor for transducing a signal into a cell and at least one amino acid residue corresponding to position 153 in the amino acid sequence of wild type human ciliary neurotrophic factor (hereinafter abbreviated as human CNTF) is substituted with another amino acid residue.

(4) A mutant protein according to (1), wherein the protein having a 4-helix bundle structure is human CNTF and at least one amino acid residue corresponding to position 153 in the amino acid sequence of wild type human CNTF is substituted with another amino acid residue.

(5) A mutant protein according to (1), wherein the protein having a 4-helix bundle structure is a leukocyte inhibitory factor (hereinafter abbreviated as LIF) and at least one amino acid residue corresponding to position 156 in the amino acid sequence of wild type LIF is substituted with another amino acid residue.

(6) A mutant protein according to (1), wherein the protein having a 4-helix bundle structure is oncostatin M (hereinafter abbreviated as OSM) and at least one amino acid residue corresponding to position 161 in the amino acid sequence of wild type OSM is substituted with another amino acid residue.

(7) A mutant protein according to (1), wherein the protein having a 4-helix bundle structure is a granulocyte colony-stimulating factor (hereinafter abbreviated as G-CSF) and at least one amino acid residue corresponding to position 146 in the amino acid sequence of wild type G-CSF is substituted with another amino acid residue.

(8) A mutant protein according to any one of (1) to (7), wherein another amino acid residue is a wild type or non-wild type amino acid residue.

(9) A mutant protein according to (8), wherein another amino acid residue is a neutral or basic amino acid residue.

(10) A mutant protein according to (9), wherein the neutral or basic amino acid residue is an aromatic amino acid residue including histidine, or an arginine residue.

(11) A mutant protein according to (10), wherein the aromatic amino acid residue including histidine is selected from tyrosine, phenylalanine, tryptophane and histidine residues.

(12) A mutant protein according to (9), wherein the neutral or basic amino acid residue is. selected from alanine, valine, leucine, isoleucine, methionine, glutamine, asparagine, glycine, proline, tyrosine, phenylalanine, tryptophane, histidine, lysine and arginine residues.

(13) A mutant protein according to (4), wherein the amino acid residue corresponding to position 63 in the amino acid sequence of wild type human CNTF is further substituted with another amino acid residue.

(14) A mutant protein according to (13), wherein the amino acid residue corresponding to position 63 is substituted with arginine residues

(15) A DNA containing the nucleotide sequence encoding the mutant protein according to any one of (1) to (14).

(16) An expression vector carrying the DNA according to (15).

(17) A procaryote or eucaryote transformed with the expression vector according to (16)

BRIEF DESCRIPTION OF DRAWING

FIG. 4 shows conditions for gene amplification in each step by PCR used in Example 1.

FIG. 5 shows primers used in Example 1, wherein the underlined portions indicate the recognition sites inserted, and symbols !, . . . and * indicate mismatching positions, a mixture of C, A, T and C, and a mixture of G and C, respectively. The nine named oligonucleotides are provided as SEQ ID NO:3 through SEQ ID NO:11, respectively.

Lane 1: molecular weight markers

Lane 2: purified wild type human CNTF expressed in *E. coli*

Lane 3: the lysate supernatant of wild type human CNTF

Lanes 4–11: the lysate supernatant of E153 mutants (4: E153R, 5: E153K, 6: E153A, 7: E153V, 8: E153L, 9: E153G, 10: E153P, 11: E153I)

Lane 12: purified wild type human CNTP expressed in *E. coli*

FIG. 7(B):

Lane 1: molecular weight markers

Lane 2: purified wild type human CNTF expressed in *E. coli*

Lane 3: the lysate supernatant of wild type human CNTF

Lanes 4–11: the lysate supernatant of E153 mutants (4: E153Y, 5: E153F, 6: E153W, 7: E153H, 8: E153M, 9: E153Q, 10: E153N, 11: E153D)

Lane 12: purified human CNTF expressed in *E. coli*

Figure 8:
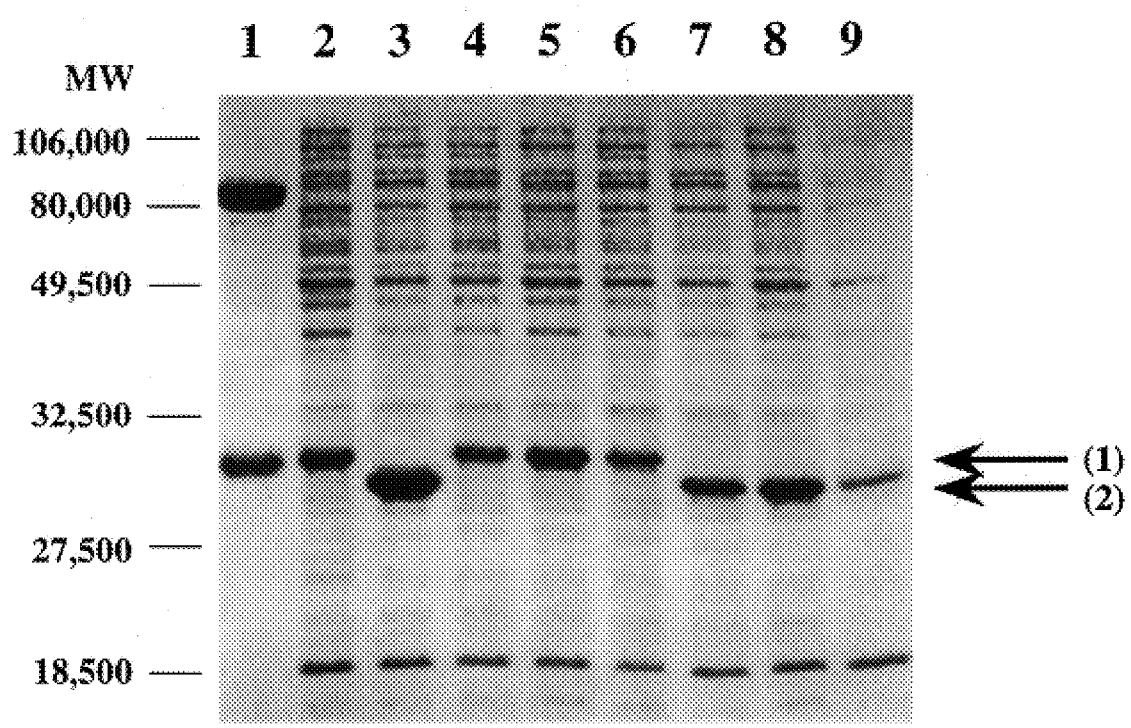

FIG. 8 indicates photographs showing the results of electrophoresis for the human CNTF mutants of the present invention obtained by SDS-PAGE, wherein each lane denotes the electrophoretic pattern of the following:

Lane 1: purified wild type human CNTF expressed in *E. coli*

Lane 2: the lysate supernatant of wild type human CNTF

Lanes 3–9: the lysate supernatant of the mutants obtained in Example 2 (3: Q63R, 4: E153R, 5: E153Y, 6: E153W, 7: E153R/Q63R; 8: E153Y/Q63R, 9: E153W/Q63R)

The mobilities of wild type human CNTF and Q63R mutant are shown by←(1) and←(2) respectively.

Figure 9:
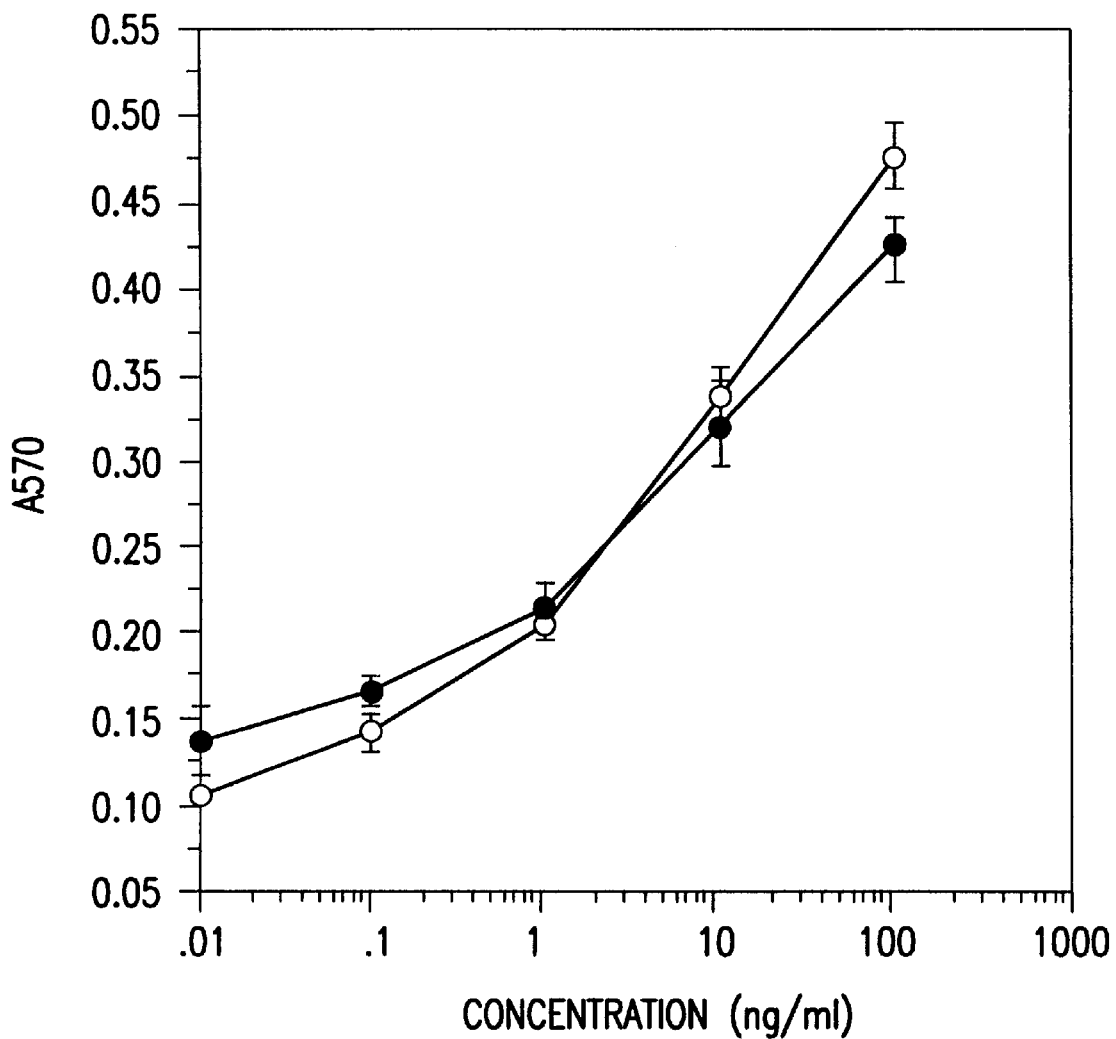

FIG. 9 shows the survival promoting activity of purified wild type human CNTF (o) expressed in *E. coli* and recombinant wild type human CNTF (●) in the *E. coli* lysate supernatant dilution on chicken DRG neurons.

Figure 10A:
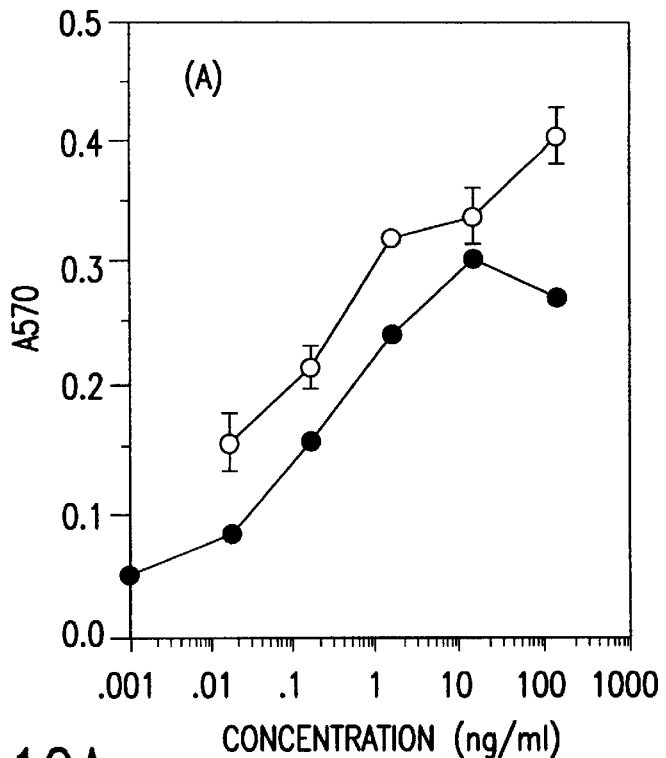
Figure 10B:
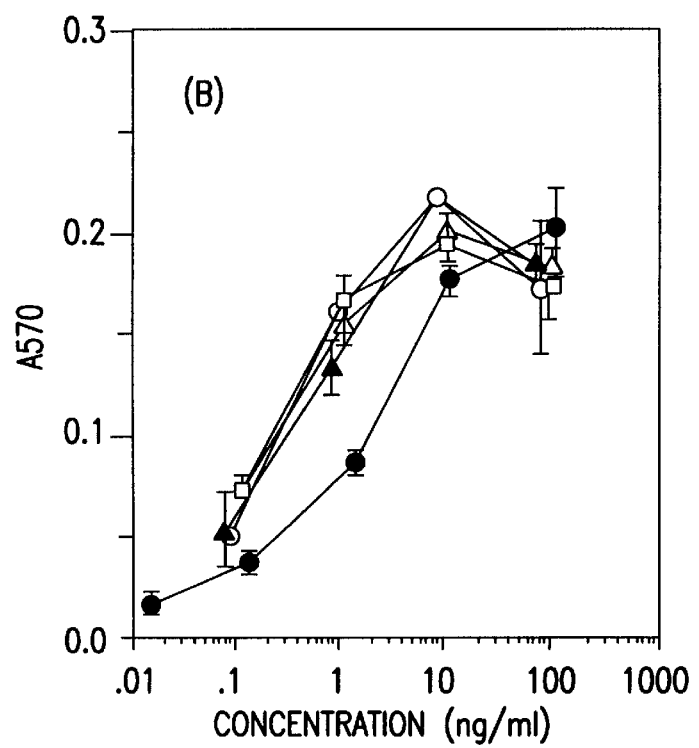

FIG. 10 shows the survival promoting activity of the E153 mutants on chicken DRG neurons; in FIG. 10(A), symbols ● and ○ denote the data for wild type human CNTF and E153R mutant, respectively; and in FIG. 10(B), symbols ●, ▲, △, ○ and □ denote the data for wild type human CNTF, E153H, E153Y, E153F and E153W, respectively.

Figure 11A:
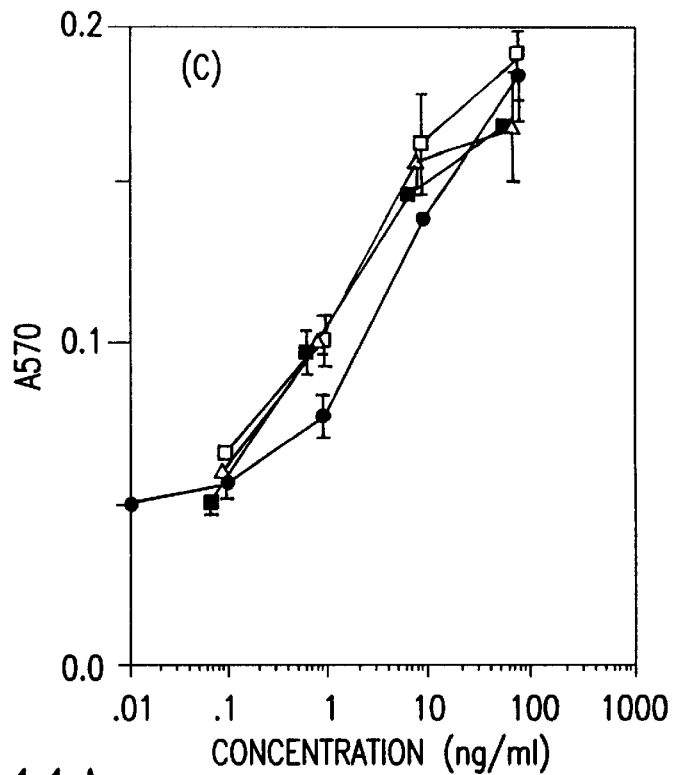
Figure 11B:
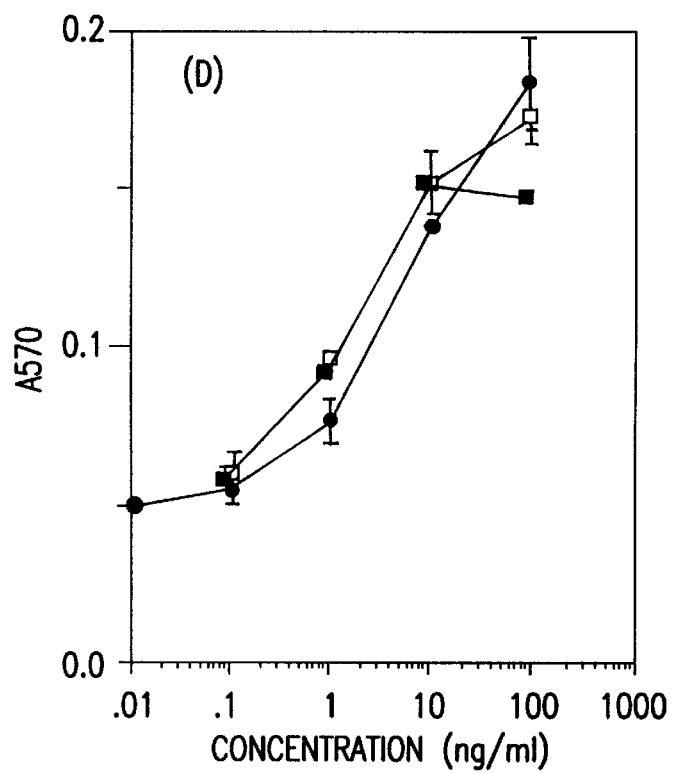
Figure 12A:
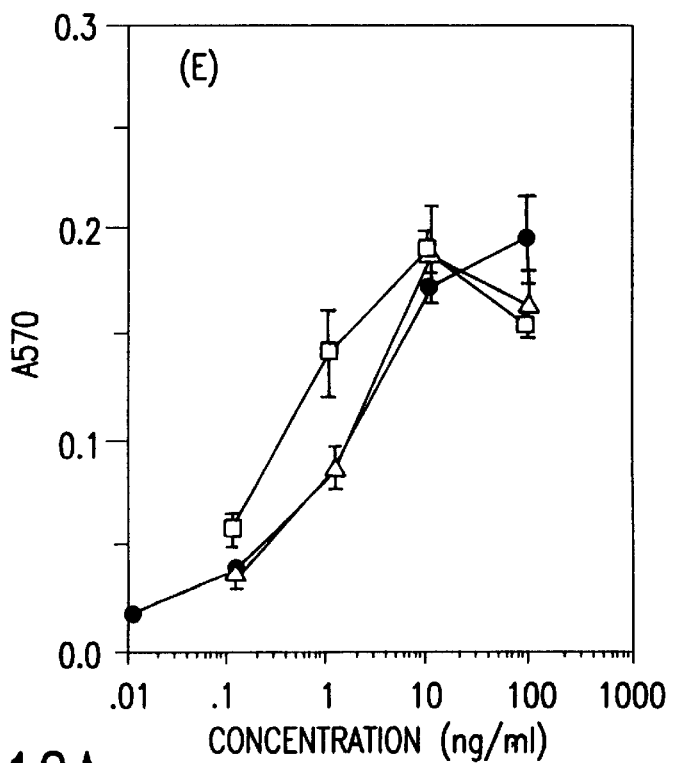
Figure 12B:
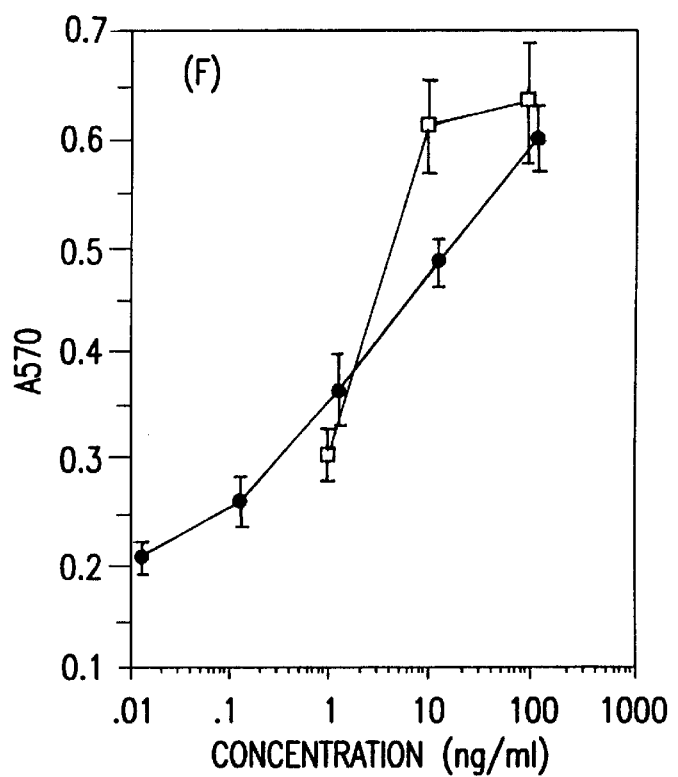

FIG. 11 shows the survival promoting activity of the E153 mutants on chicken DRG neurons; in FIG. 11(C), symbols ●, □, ■ and △ denote the data for wild type human CNTF, E153A, E153V and E153L, respectively; and in FIG. 11(D), symbols ●, □ and ■ denote the data for wild type human CNTF, E153G and E153P, respectively FIG. 12 shows the survival promoting activity of the E153 mutants on chicken DRG neurons; in FIG. 12(E), symbols ●, □ and ∆ denote the data for wild type human CNTF, E153M and E153I, respectively and in FIG. 12(F), symbols ● and □ denote the data for wild type human CNTF and E153K mutant.

Figure 13:
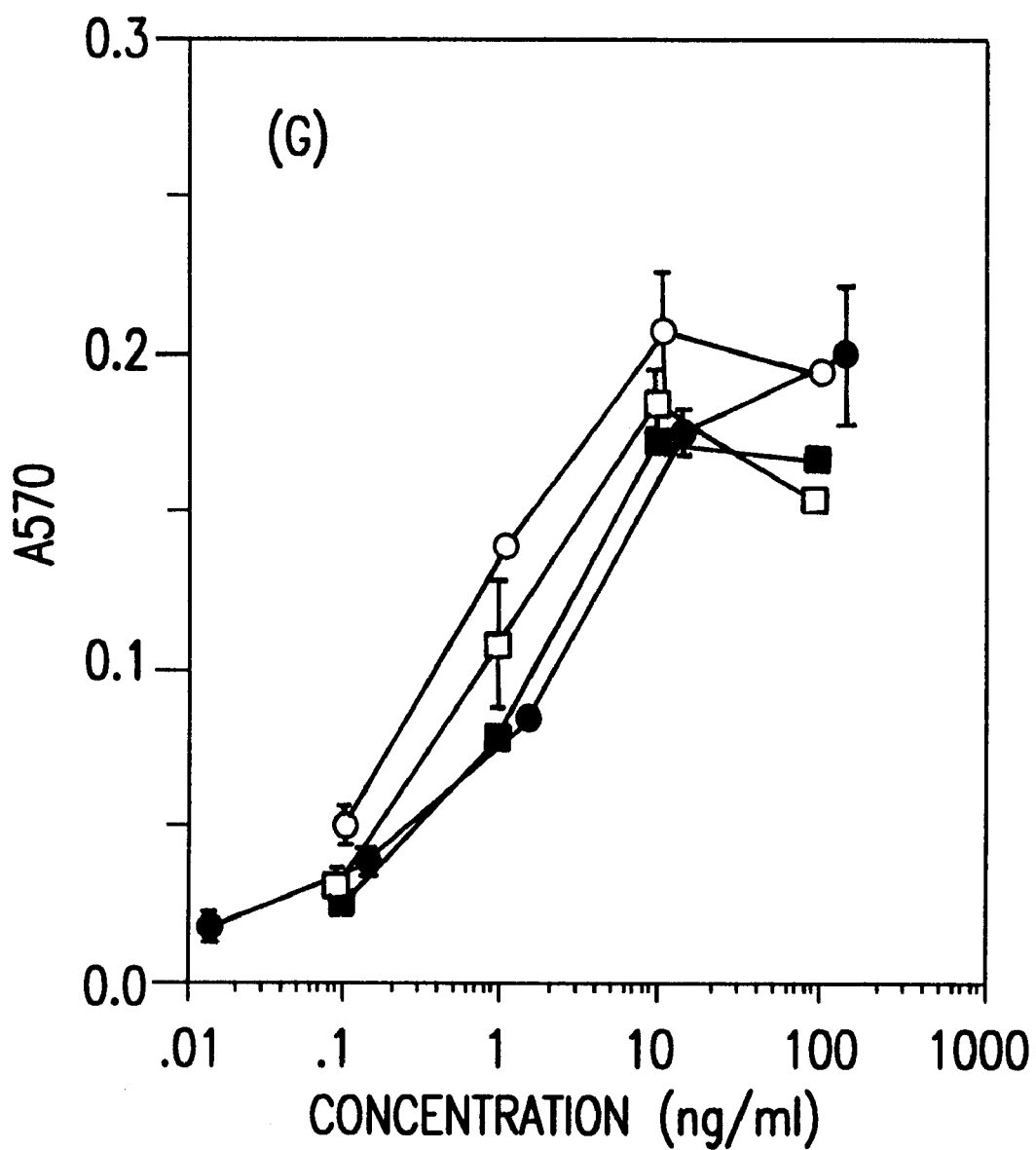

FIG. 13 shows the survival promoting activity of the E153 mutants on chicken DRG neurons; in FIG. 13(G), symbols ●, ○, □ and ■ denote the data for wild type human CNTF, E153Q, E153N and E153D, respectively.

Figure 14A:
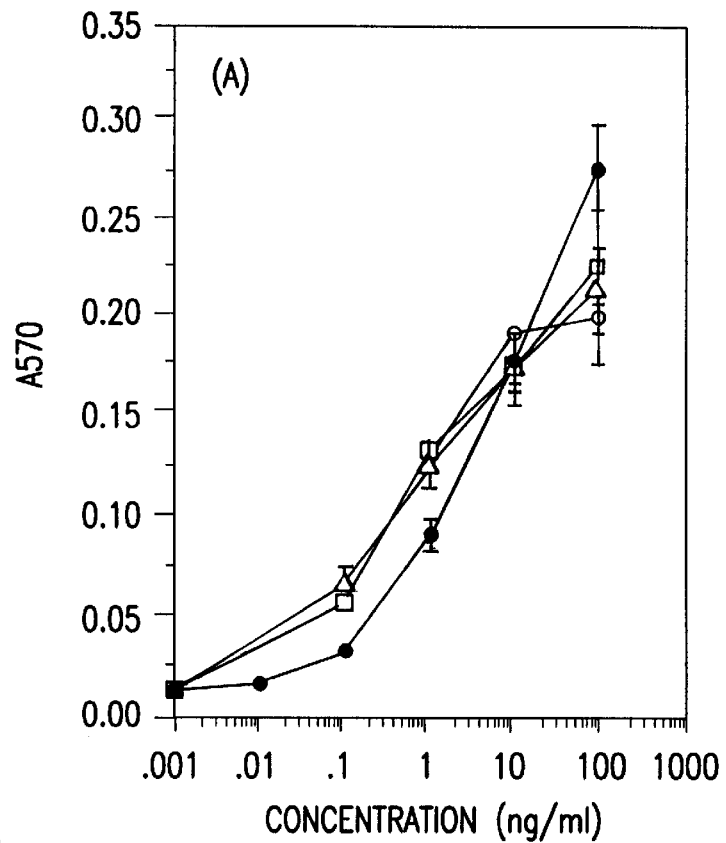
Figure 14B:
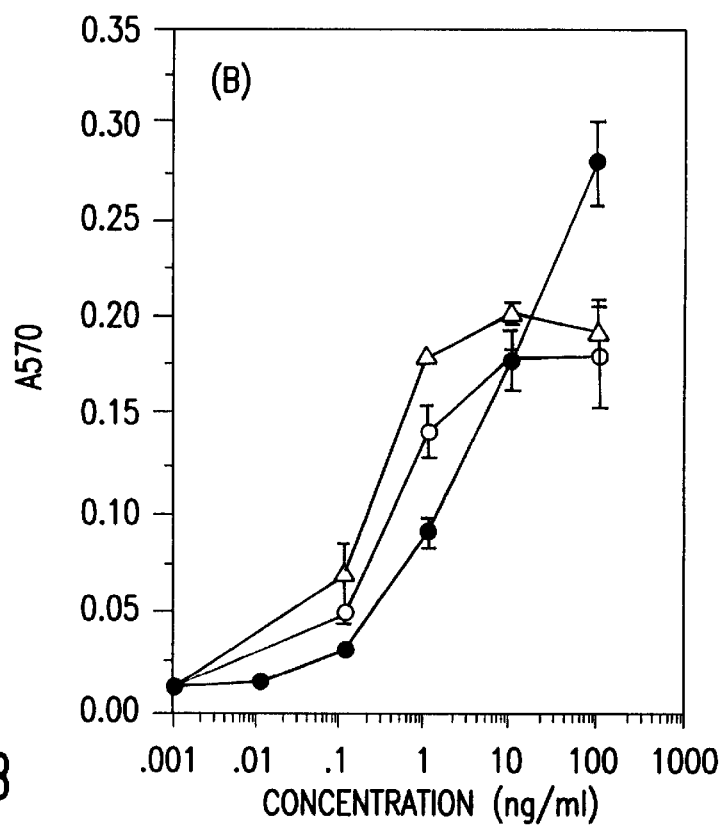

FIG. 14 shows the survival promoting activity of the E153 mutants on chicken CG neurons; in FIG. 14(A), symbols ●, ○, ∆ and □ denote the data for wild type human CNTF, E153R, E153Y and E153F, respectively and in FIG. 14(B), symbols ●, ∆ and ○ denote the data for wild type human CNTF, E153H and E153W, respectively.

Figure 15A:
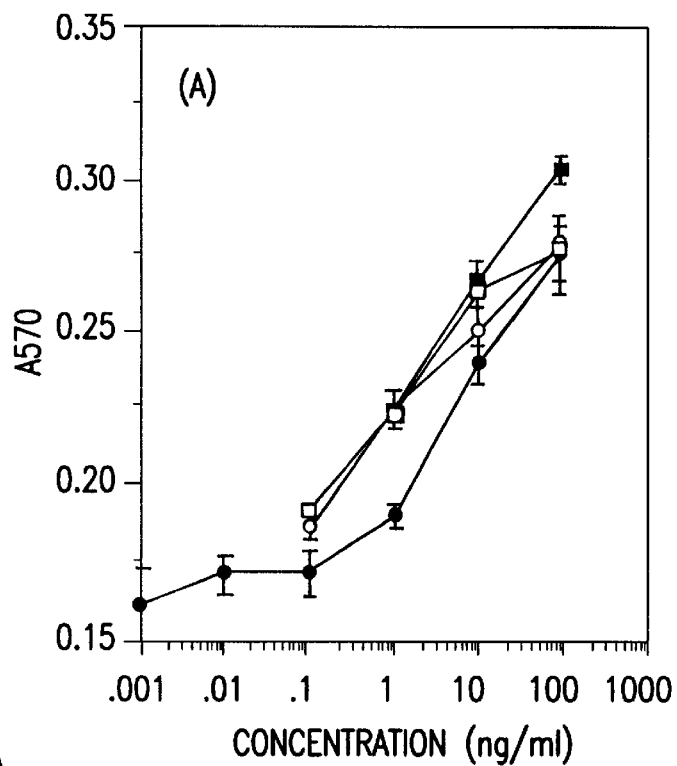
Figure 15B:
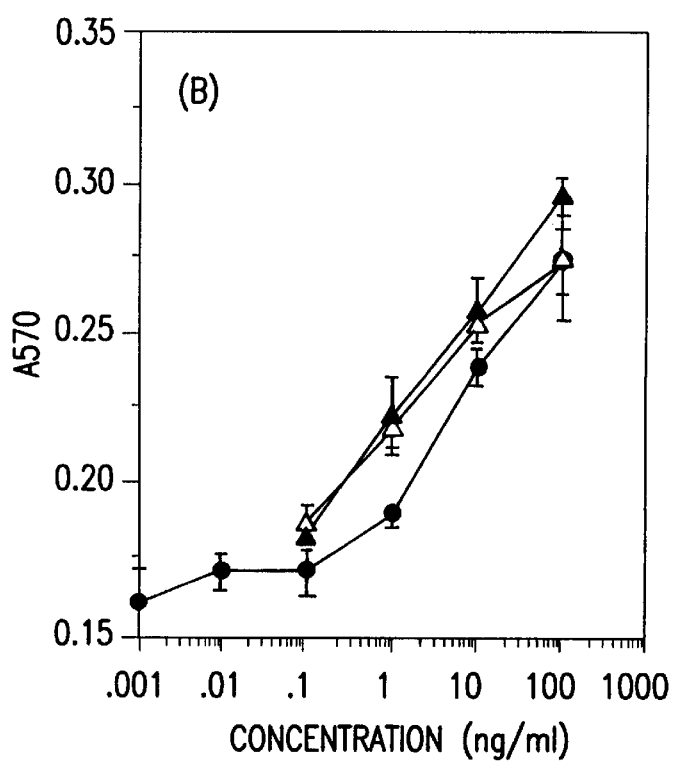

FIG. 15 shows the survival promoting activity of the E153 mutants on rat DRG neurons; in FIG. 15(A), symbols ●, ○, □ and ■ denote the data for wild type human CNTF, E153R, E153Y and E153F, respectively and in FIG. 15(B), symbols ●, ∆ and ▲ denote the data for wild type human CNTF, E153H and E153W, respectively.

Figure 16:
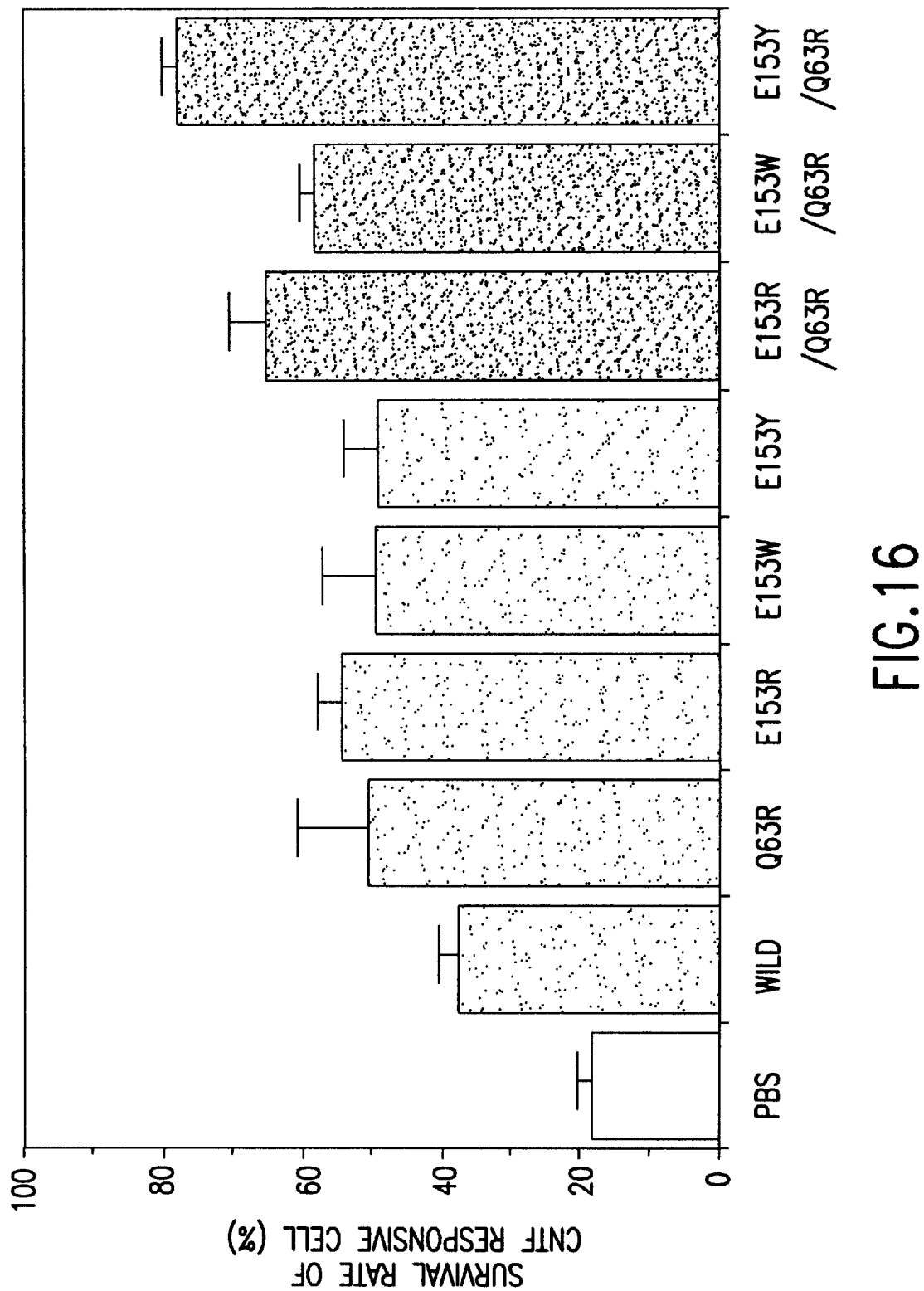

FIG. 16 shows the activity of wild type human CNTF and the CNTF mutants on the survival promotion of chicken DRG neurons, when they were added in a final concentration of 1 ng/ml, wherein the ordinate represents a survival rate (%) of CNTF responsive cell which is expressed by a percentage of absorbance at 570 nm of the formed formazan, when the absorbance of the formazan formed by 100 ng/ml of CNTF or CNTF mutant is made 100% (in this experiment, $A_{570}$=0.19 was made 100%).

Figure 17:
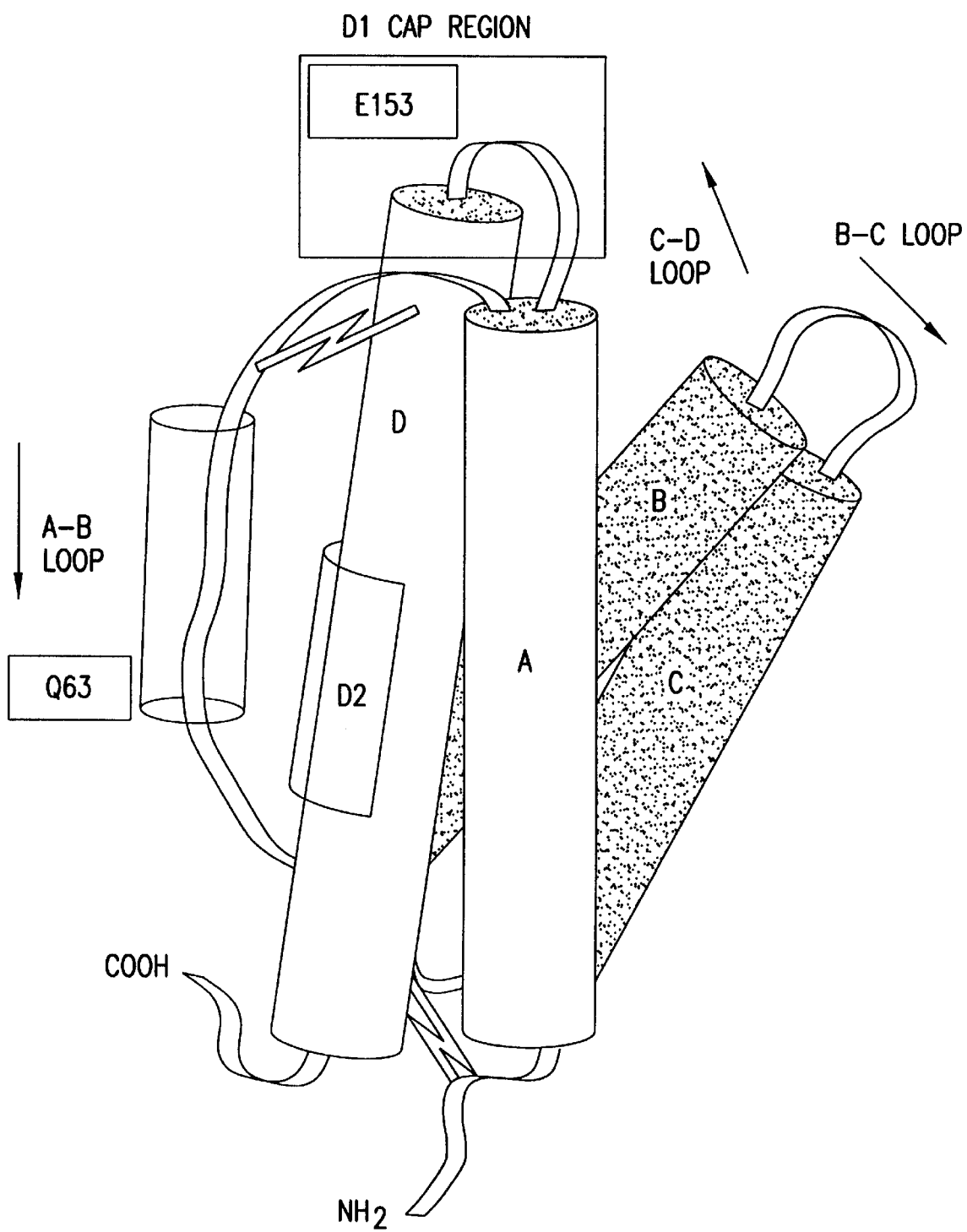

FIG. 17 shows a three-dimensional conformation of human growth hormone (hGH), on which the transduced segments (D1 cap regions E153 and Q63) in the human CNTF mutant of the present invention are indicated.

Figure 18:
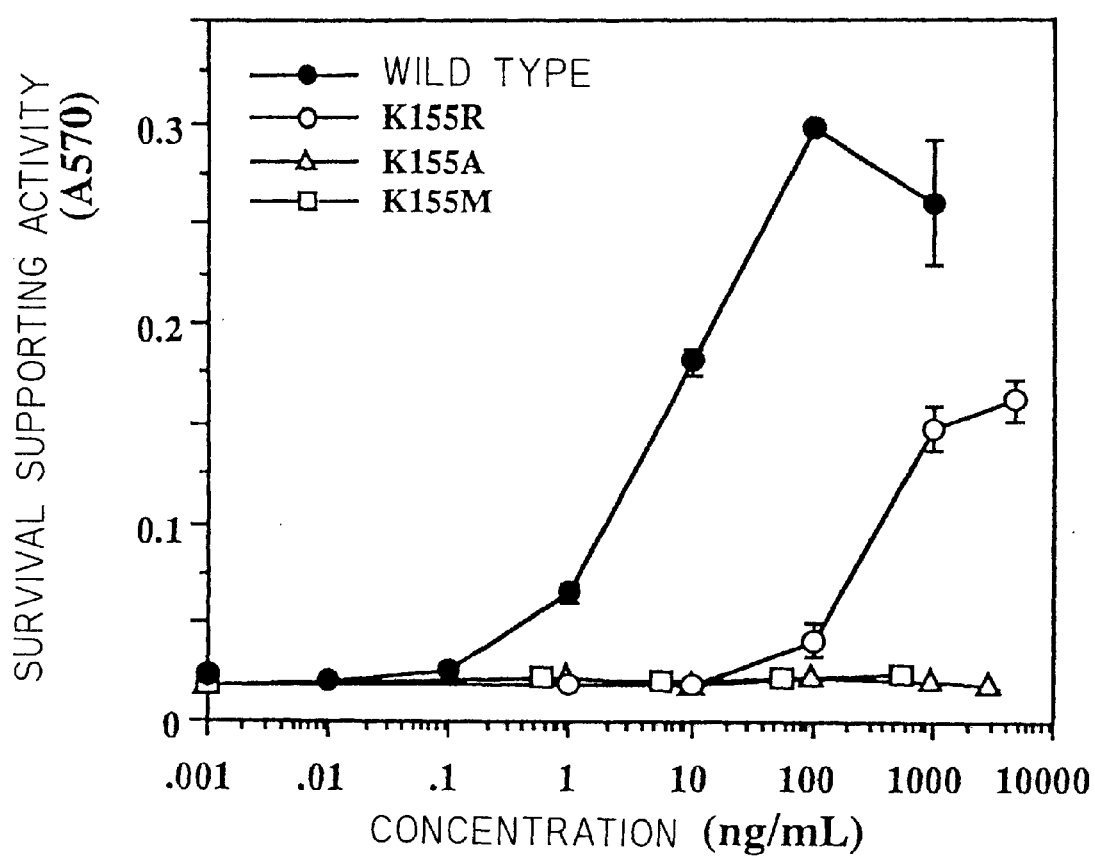

FIG. 18 shows the survival promoting activity of the E155 mutants on chicken DRG neurons, wherein symbols ●, ○, ∆ and □ denote the data for wild type human CNTF, K155R, K155A and K155M, respectively.

Figure 19:
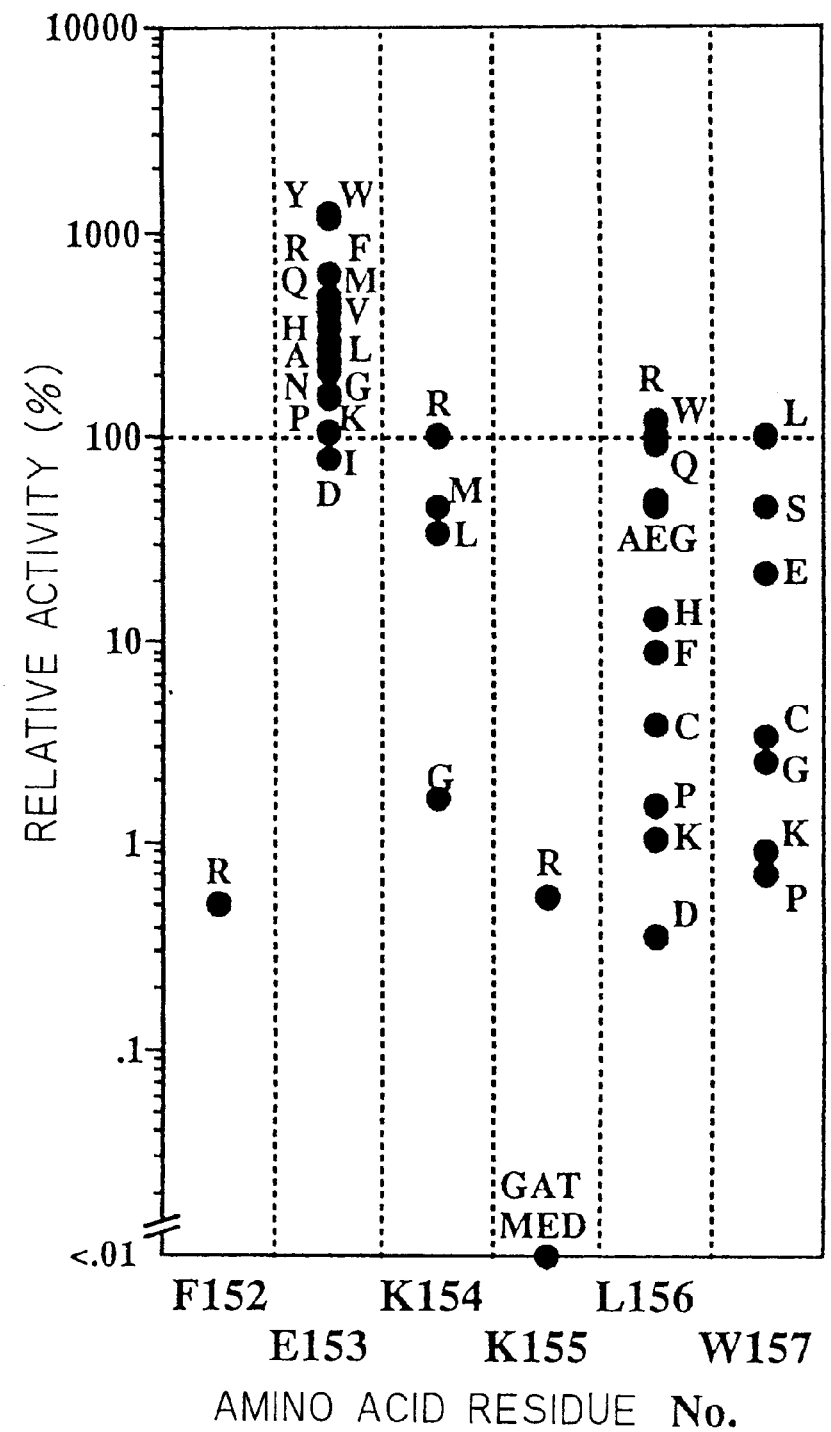

FIG. 19 shows the survival promoting activity of the human CNTF mutants in the D1 cap region on chicken DRG neurons, wherein symbol ● denotes each mutant and a relative activity (%) to wild type human CNTF is shown in terms of 50% effective concentration (EC50).

FIG. 20 is a brief summary of known results of the structure-activity relationship analyses on the proteins belonging to the long chain group in α-helical cytokines, or the region predictable to play a role for their biological activity.

In FIG. 20, (A) is a group of proteins that utilize gp130 for signal transduction, and (B) is a group of the proteins that utilize other receptors. The region empirically known to be responsible for the activity expression is shown by a dotted area and the region predicted to be associated with the activity expression is shown by a frame formed with a dashed line. The analysis of each protein on the structure-activity relationship is reported in the following publications: R. Savino et al., Proc. Natl. Acad. Sci. U.S.A., 90, 4067 (1993); C. Lutticken et al., FEBS Lett., 282, 265 (1991); J. P. J. Brakenhoff et al., J. Immunol., 145, 561 (1990), X. Li et al., J. B. C., 268, 22377 (1993); B. C. Cunningham et al., Science, 247, 1461 (1990); A. M. Devos et al., Science, 255 306 (1992); J. P. J. Brakenhoff et al., J. B. C., 269, 86 (1994); R. C. Robinson et al., Cell, 77, 1101 (1994); J. C. Kallestad et al., J. B. C., 266, 8940 (1991); I. Kawashima et al., FEBS Lett., 283, 199 (1991); V. Goffin et al., Eur. J. Biochem., 214, 199 (1993); B. Lovejoy et al., J. Mol. Biol., 234, 640 (1993); D. Wen et al., J. B. C., 269, 22839 (1994); and, B. F. Cheethan et al., Antiviral Res., 15, 27 (1991).

BEST MODE FOR CARRYING OUT THE INVENTION

In the present invention, the amino acid sequence for naturally occurring human CNTF is shown by the amino acid sequence SEQ ID NO:1 disclosed in WO 91/4316 Accordingly, the position of an amino acid used throughout the specification is designated in such a manner that is indicated in WO 91/4316.

In the present invention, the term "mutant" is used to mean a protein in which at least a part of the amino acid sequence of a wild type protein has been artificially modified.

In the present invention, the term "human CNTF mutant" is used to mean a protein artificially modified in at least a part of the amino acid sequence which encodes the aforesaid naturally occurring human CNTF. More specifically, the human CNTF mutant refers to a mutant in which at least the amino acid (glutamic acid) residue corresponding to position 153 in the amino acid sequence of wild type human CNTF is substituted with another amino acid residue. Herein, the term "another amino acid residue" is used to mean a wild type amino acid residue or a non-wild type amino acid residue. Where a wild type residue is used as another amino acid residue, the residue is preferably a neutral or basic amino acid residue. That is, it is preferred for the human CNTF mutants in the present invention that the amino acid residue corresponding to position 153 in the amino acid sequence of wild type human CNTF is substituted with a residue of neutral amino acid such as alanine, valine, leucine, isoleucine, methionine, glutamine, asparagine, glycine, proline, serine, threonine, cysteine, tyrosine, phenylalanine or tryptophane; or with a residue of basic amino acid such as histidine, lysine or arginine.

Among them, it is particularly preferred from a viewpoint of improving a specific activity that the amino acid residue at position 153 is substituted with a residue of aromatic amino acid such as tyrosine, phenylalanine, tryptophane or histidine, or with arginine residue. In additions a residue of hydrophobic amino acid such as alanine, valine, leucine, methionine or proline is also preferable for the substitution.

Examples of the case where a non-wild type amino acid residue is used as another amino acid residue include a case in which a non-wild type amino acid is used for the substitution during the course of synthesis of a protein and a case in which a wild type amino acid residue introduced is chemically modified after protein synthesis. For introducing a non-wild type amino acid residue during the synthesis of a protein, there is known a method generally effective for introducing the non-wild type amino acid residue site-specifically (Science, 244, 182 (1989)); as the results are reported therein, tRNA is chemically acylated with fluorine- or nitro-modified phenylalanine at the para-position and the acylated tRNA is expressed in vitro protein synthesis system Another method comprises introducing furanomycin, which is a non-wild type amino acid, into a desired site utilizing isoleucyl-tRNA of E. coli capable of recognizing furanomycin (J. B. C. 265, 6931 (1990)). In still another method, the objective amino acid residue is substituted with a non-wild type amino acid in a cell-free protein synthesis system (J. Biochem., 110 166 (1991)). Still another method comprises chemical modification of a purified protein amino acid residue-specifically or site-specifically (SHIN SEIKA-GAKU JIKKEN KOZA (Lecture Series on New Biochemical Experiments), 1, IV, 11 (1991)). The mutant protein may also be obtained, for examples by amidation of the glutamic acid residue at position 153; substitution of the glutamic acid residue at position 153 with lysine residue followed by trinitrophenylation; substitution of the glutamic acid residue at position 153 with arginine residue followed by reaction with phenylglyoxal; substitution of the glutamic acid residue at position 153 with histidine residue followed by carbethoxylation; substitution of the same residue with tryptophane residue followed by reaction with an arylsulfenyl chloride; or substitution of the same residue with tyrosine residue followed by nitrations These chemical modifications may be performed in a conventional manner.

In the present inventions in addition to the substitution of the amino acid residue corresponding to the position 153 of wild type human CNTF, the amino acid residues located at positions other than the position 153 may also be modified (including substitution, deletion and addition of an amino acid(s) and a domain replacement) in such a manner as generally accepted in the field of protein engineering so long as the activity of human CNTF is not seriously ruined. The mutants include, in addition to those in which the position 153 has been substituted those substituted with another amino acid residue, e.g., at positions 63, 136, 154, 156, 157, 160, 163 164, 167, 177, 178 and 184. The substitution of an amino acid residue(s) located other than at position 153 is effected with "another amino acid residue" as defined hereinabove.

It is already reported that when the amino acid residue at position 63 in the amino acid sequence encoding wild type human CNTF is substituted with arginine residues the CNTF activity increases (Panayotatos et al., J. B. C., 268, 19000–19003 (1993)). A combination of such mutations on human CNTF, each of which is effective for enhancing the CNTF activity can provide the mutant having a specific activity higher than the activity of the single mutant at one position. For example, where the substitution occurs on the amino acid residue at both position 153 and position 63, preferred examples of the resulting double mutant are the mutant substituted with arginine at positions 153 and 63, the mutant substituted with tyrosine at position 153 and with arginine at position 63, and the mutant substituted with tryptophane at position 153 and with arginine at position 63.

In other α-helical cytokines having structural similarity to human CNTF, it is predicted that the site corresponding to the D1 cap region would take part in the activity expression, as in the case of human CNTF because of their structural similarity and because IL-6; LIF, OSM and IL-11 utilize the same receptor in common. Particularly in the mutation of the D1 cap region, it is highly likely that a mutant having a higher specific activity than in wild type human CNTF will be obtained when the mutation is designed to occur on the amino acid residue corresponding to 153 amino acid of human CNTF. Therefore, it is considered that these mutant proteins expected to be obtained would solve the problem of a large dose administration, which comes in question upon development of a wild type protein for medical use.

The mutant protein of the present invention can be constructed by a method conventionally used in the field of genetic engineering Such a conventional method will be explained below with reference to the human CNTF mutant. Where the amino acid residue corresponding to position 153 is substituted with a wild type amino acid residue, the method comprises replacing with a synthetic oligonucleotide a part of a vector bearing DNA encoding wild type human CNTF or the human CNTF mutant to convert the DNA encoding glutamic acid corresponding to position 153 in the amino acid sequence of wild type human CNTF with a DNA encoding another amino acid, ligating the DNA with an appropriate expression vector, transfecting the expression vector to a host and producing the objective human CNTF mutant in the transfected host. The method is described below in more detail.

To construct the human. CNTF mutant of the present invention, there may be employed, for examples a human CNTF structural gene encoding wild type human CNTF. The human CNTF structural gene encoding wild type human CNTF has already been acquired by cloning from, e.g., human genomic DNA (K. A. Stockli et al., Nature, 342, 316 (1989) L. F. Lin et al., Science, 246, 1023 (1989), P. Masiakowski et al., J. Neurochem., 57, 1003 (1991), A. Negro et al., Eur. J. Biochem. 201, 289 (1991), J. R. McDonald et al., Biochem. Biophys. Acta, 1090, 70 (1991) and A. Lam et al., Gene, 102, 271 (1991)). The DNA sequence and amino acid sequence of the human CNTF structural gene are also known. Accordingly, the structural gene of wild type human CNTF can be cloned in a conventional manner (J. Sambrook et al., Molecular Cloning: A Laboratory Manual).

A method for replacing with another sequence a specific sequence in the cloned structural gene of wild type human CNTF in plasmid is now generally available. In the present invention, the amino acid residue corresponding to position 153 of wild type human CNTF may be likewise substituted with another amino acid residue in such a known manner. It is advantageous to perform the substitution by amplifying a DNA encoding the objective substituted amino acid sequence and replacing the resulting DNA fragment for the sequence (hereinafter referred to as the corresponding sequence) at the site to be substituted in wild type human CNTF.

Specifically, the substitution proceeds in a convenient way by using as primers an oligonucleotide comprising, e.g., the substituted nucleotide sequence and an oligonucleotide corresponding to the nucleotide sequence which is not the substitution site or the sequence of a vector segment in the sequence of human CNTF required for amplifications amplifying the region inserted between the two primers using as a template a plasmid carrying the structural gene of wild type human CNTF, and replacing the amplified fragment with the corresponding sequence of wild type human CNTF. For amplification of the region between the two primers, it is advantageous to use, e.g., gene amplification known as PCR (Genes 77, 61–68 (1989)). For the gene amplification (PCR), there may be advantageously employed a DNA automated amplification device commercially available. Where one amplification is insufficient to obtain a fragment having an adequate restriction site for the substitution with the corresponding sequence of wild type human CNTF, the product obtained by the first gene amplification may also be employed as one of the primers for the second gene amplification to prepare a fragment having a desired restriction site.

Figure 3:
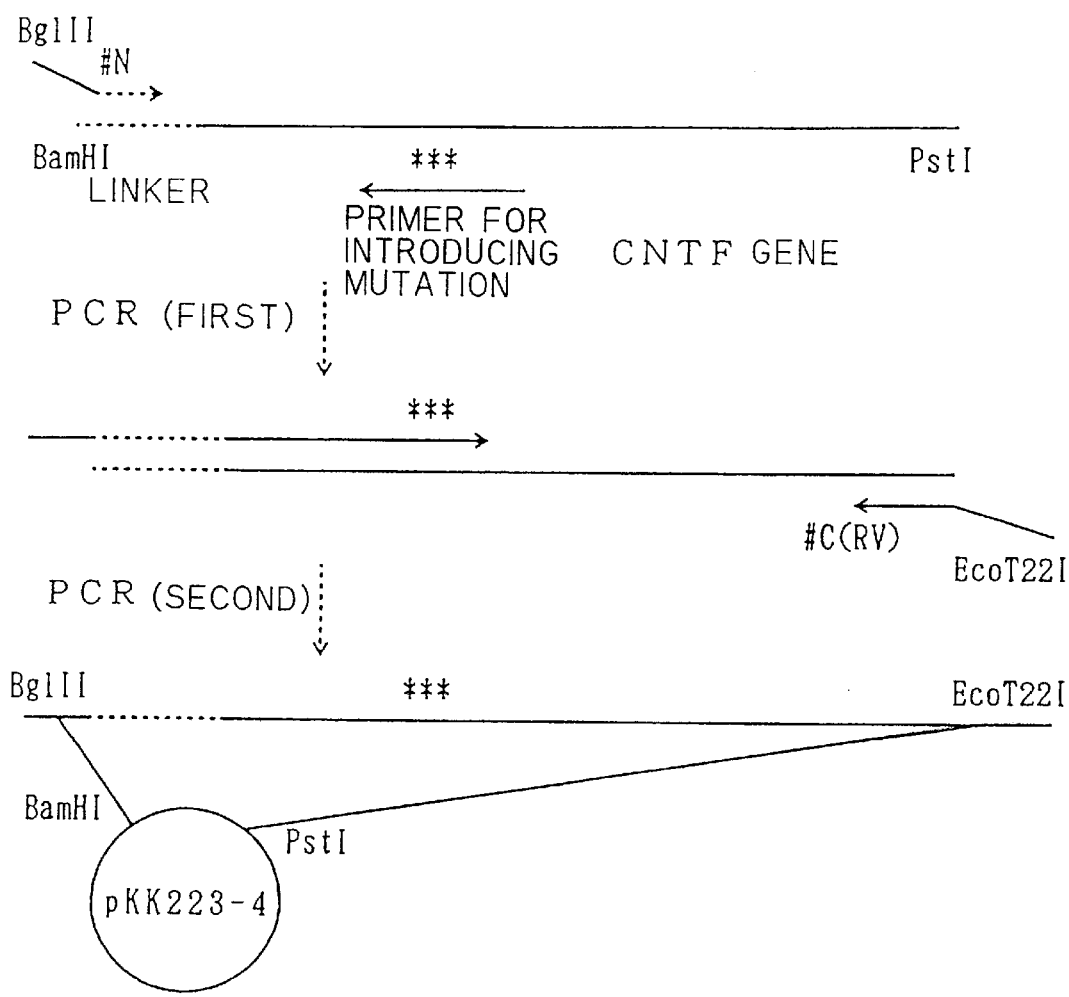
FIG. 3 shows an outlined method for construction of an expression vector for the human CNTF mutant of the present invention by gene amplification (PCR).

That is, as shown in FIG. 3, the gene amplification is conducted twice so that the objective substituted nucleotide sequence has been introduced and a fragment having a restriction site advantageous for the substitution with the corresponding sequence of natura human CNTF can be obtained. Where the two different sites are substituted mutation is introduced independently at the respective sites and cloning is then performed utilizing an appropriate restriction site to construct a gene having the double mutations.

Alternatively, after the first mutation has been introduced into one position, the mutated gene is used as a template and the second mutation is introduced by gene amplification to construct a gene having the double mutations.

In order to confirm the DNA sequence in which the desired substitution or insertion has been achieved, it is advantageous to use, e.g., Sequenase DNA Sequence Kit (Toyobo Co. Ltd.) utilizing the principle of dideoxy method described in Science, 214, 1205 (1981). Other procedures for genetic manipulation used in the Examples, including digestion of DNA with restriction enzymes, deletion of DNA, separations recovery or ligation of the resulting DNA fragments are all performed by a modification of the known method described in T. Maniatis et al., Molecular Cloning, A Laboratory Manuals Cold Spring Harbor Lab. (1982).

Figure 1:
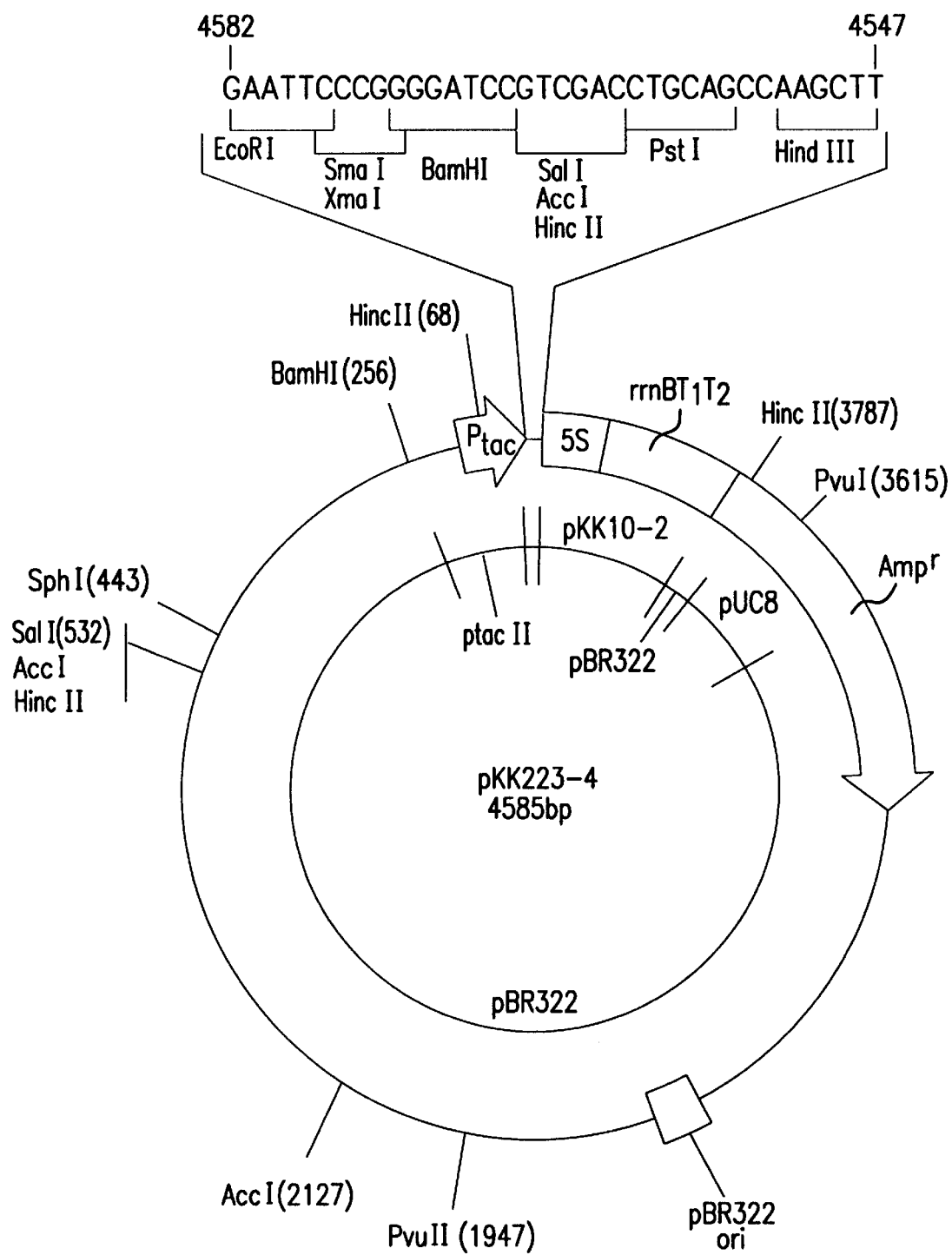
FIG. 1 shows the structure of vector pKK223-4 used to construct an expression vector for the human CNTF mutant of the present invention. The nucleotide sequence at the top of the figure is as set forth in SEQ ID NO:2.

The thus obtained DNA carrying the nucleotide sequence which encodes the human CNTF mutant is ligated with a well known expression vector such as pKK223-4 (Pharmacia Inc., FIG. 1) and then transfected to an appropriate host cell to express the human CNTF mutant which is the objective product of the present invention. Any of eucaryotes and procaryotes may be used as a host cell. $E.$ $coli$ and mammalian cell line are widely available and readily accessible, unless otherwise indicated A typical example of $E.$ $coli$ is a strain of JM109. As the mammalian host cell, there are known COS-1 and CHO cells.

For transfection to these host cells using an expression vectors it is advantageous to adopt the electric pulse method as described in S. Takayama, SAIBO KOGAKU (Cell Engineering), 6, 771 (1987) or the calcium chloride method as described in J. Mol. Biol., 53, 159 (1970). Using the $E.$ $coli$ transformant or mammalian cell line, the human CNTF mutant protein can be expressed in a conventional manner as described in T. Maniatis et al., Molecular Cloning: A Laboratory Manual, Cold Spring Harbor Lab. (1982). The obtained cells may be lysed in a conventional manner and the lysate may be centrifuged, e.g., at 10500×g to obtain a soluble fraction. The soluble fraction contains the human CNTF mutant in such a concentration that is usable for assaying various activities, without or with an appropriate dilution. The thus expressed human CNTF mutant protein may be purified, if necessary in a conventional manner as described in J. Neurochem., 57, 1003 (1991).

In more detail after the expression and induction, $E.$ $coli$ is collected lysed by lysozyme treatment and then sonicated. Centrifugation is performed at 11000×g to obtain an insoluble fraction containing the human CNTF mutant protein. The fraction is solubilized in 6M guanidine hydrochloride solution and the solution is dialyzed to Tris-hydrochloride buffer containing β-mercaptoethanol for regeneration. Thereafter the dialysate is applied to anionic exchange column chromatography (Asahipak-502NP, Asahi Chemical Co., Ltd.). The solubilized human CNTF mutant protein is eluted by NaCl linear concentration gradient. The eluted soluble protein is applied to hydrophobic column chromatography (Ether-5PW, Toyo Soda Mfg. Co., Ltd.). After washing the column, elution is performed by ammonium sulfate linear concentration gradient to obtain purified human CNTF mutant protein. These procedures are partially modified from those described in J. Neurochem., 57, 1004–1005 (1991).

In order to quantitatively determine the expressed human CNTF mutant, an anti-human CNTF antibody may be prepared as described below and utilized for the determination. That is, using the purified wild type human CNTF protein prepared as described above, an animal such as a male New Zealand white rabbit weighing 1 kg may be immunized in a conventional manner as described in methods in Enzymology, 73, 46–52 (1981) to collect antisera. The anti-human CNTF antibody can be purified from the antisera by column chromatography using a column carrier such as activated Sepharose (Pharmacia Inc., CNBr Activated Sepharose) on which authentic purified wild type human CNTF is fixed. The use of the specific anti-human CNTF antibody thus obtained may permit enzyme immunoassay (ELISA) for quantitative determination of the human CNTF mutant; in this cases even a trace amount of the human CNTF mutant protein is sufficient for the quantitative determination, though the mutant protein is in a non-purified state.

Another method for quantitative determination of the human CNTF mutant comprises utilization of SDS polyacrylamide gel electrophoresis (SDS-PAGE) SDS-PAGE is performed by a known manner as described in Nature, 227, 680 (1970). Then, the concentration of the gel band derived from CNTF is processed using an image processing software (e.g., NIH Image 1.47). The human CNTF mutant protein may be likewise quantitatively assayed even in a non-purified state, as assayed by ELISA.

The biological activity of the human CNTF mutant protein constructed as described above may be assessed by a known method as described in Nerve Growth Factors, 31–56 (1989), using, e.g., chicken dorsal root ganglion (DRG), ciliary ganglion (CG) or rat DRG neurons. As will be described in the Examples hereinbelow, where the amino acid residue at position 153 has been substituted with a residue of alanine, valine, leucine, methionine, glutamine, asparagine, glycine, proline or lysine, the survival promoting activity on chicken DRG neurons is higher by 2 to 3 times than that of wild type human CNTF in which position 153 remains unsubstituted as glutamic acid. The mutant in which the amino acid residue at position 153 has been substituted with a residue of tyrosine, phenylalanine, tryptophane, histidine or arginine displays the survival promoting activity on chicken DRG neurons, chicken CG neurons and rat DRG neurons higher by approximately 10 times than that of wild type human CNTF. Where the amino acid residues at positions 153 and 63 have been substituted with another amino acid residue (e.g., a residue of arginine, tyrosine or phenylalanine) and arginine residue, respectively, the double mutant shows a much higher specific activity on chicken DRG neurons than that of the single mutant substituted at either position.

As described above, the human CNTF mutant of the present invention possesses the biological activity comparable or even superior to that of wild type human CNTF. Therefore, as is wild type human CNTF, the human CNTF mutant of the present invention is effective for the treatment of diseases caused by peripheral nerve disorders such as disease caused by denaturation of motor neurons, peripheral nerve neuropathy, etc.; central nerve disorders such as Alzheimer's disease, cerebrovascular dementia, Parkinson's disease, Huntington's disease, etc.; diseases caused by disorders of optic neurons such as retinitis pigmentosa, glaucoma, diabetic retinopathy, retinitis macula lutea, etc. Furthermore it is expected that the human CNTF mutant of the present invention would eliminate the problems which have arisen during the development of wild type human CNTF as a medicament, e.g., the problem caused by a large dose administration, difficulty in controlling the production of wild type human CNTF in a necessary amount, side effects due to impurities, or side effects caused by appearance of an autoantibody to human CNTF itself.

Hereinafter the present invention will be described more specifically by referring to Examples and Comparative Examples but is not deemed to be limited thereto. The abbreviations used in the Examples are shown below.

PCR: polymerase chain reaction
BAP: bacterial alkaline phosphatase
ELISA: enzyme-linked immunosorbent assay
IPTG: isopropyl-β-D-thiogalactopyranoside
PMSF: phenylmethanesulfonyl fluoride
PBS: phosphate buffered saline
BSA: bovine serum albumin
ALP: alkaline phosphatase
SA: streptoavidin
PNPP: p-nitrophenyl phosphate
DRG: dorsal root ganglion
DMEM: Dulbecco's modified Eagle's medium
FCS: fetal calf serum
MTT: 3-[4,5-dimethylthiazol-2-yl]-2,5-diphenyltetrazolium bromide
CG: ciliary ganglion

EXAMPLE 1

Figure 2:
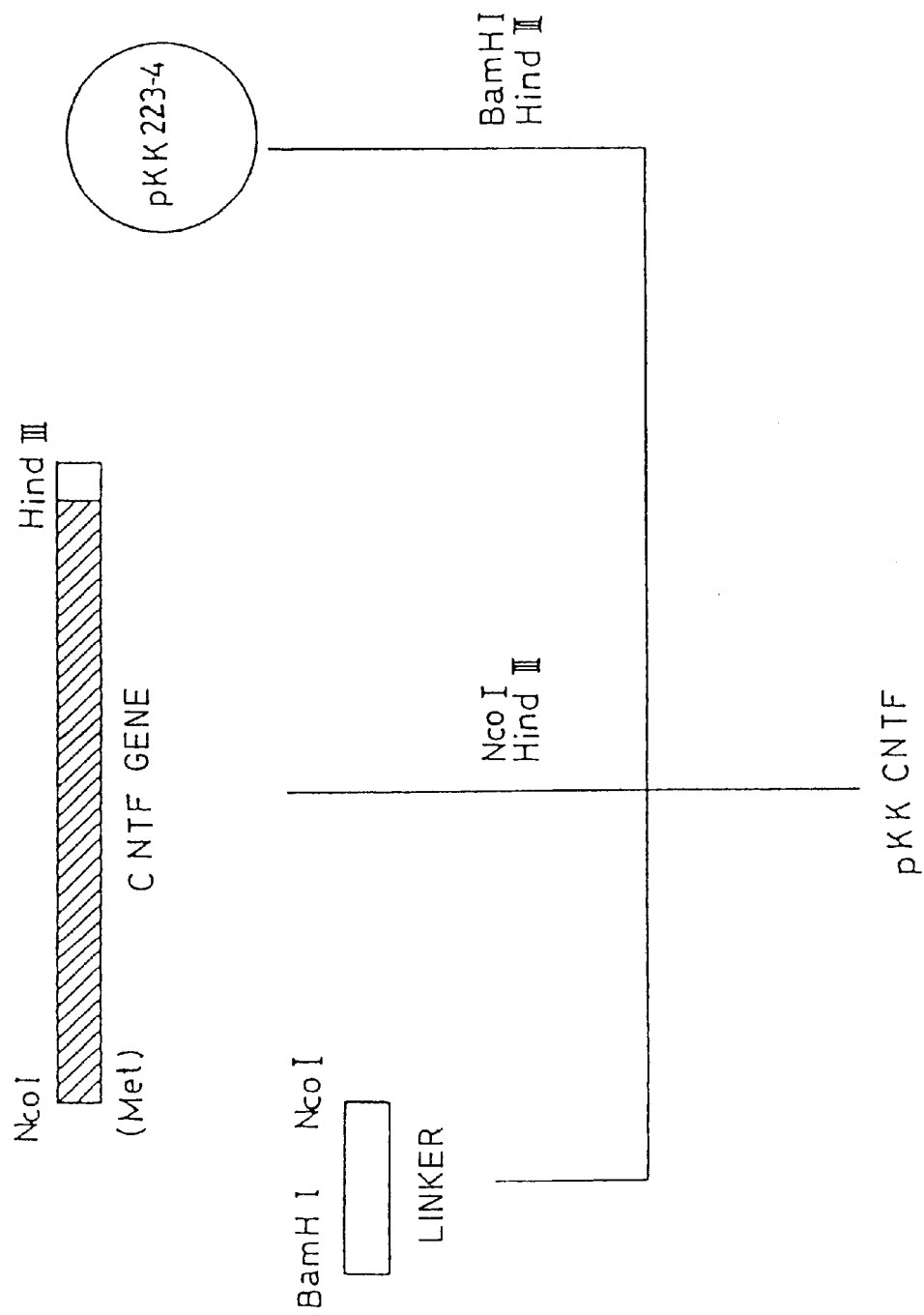
FIG. 2 shows construction of wild type human CNTF expression vector pKKCNTF.

Introduction of mutation into natural human CNTF and preparation of a vector for expression of human CNTF mutant 1) Material E. coli JM109 (lacIQ: Takara Shuzo CO., Ltd.) was used as a host cell for cloning and for expression of wild type human CNTF and human CNTF mutant. As an expression vector for wild type human CNTF, there was pKKCNTF prepared by integrating wild type human CNTF gene into E. coli expression vector pKK223-4 (Pharmacia Inc., FIG. 1) containing tac promoter and a linker DNA into the CNTF gene at the 5' end (FIG. 2).

2) Amplification of the gene into which mutation has been introduced

Site-specific mutation of a random amino acid was introduced by gene amplification through PCR. PCR was carried out in two steps as shown in FIG. 3. Reaction conditions for PCR in each step are shown in FIG. 4. For PCR, wild type human CNTF expression vector pKKCNTF was used as a template and pfu polymerase (Stratagene) having a high fidelity was utilized as a polymerase. Three synthetic DNA primers designated as #N, #C(RV) and pE153 in FIG. 5 were used as primers. The amino acid sequences of these primers are shown in FIG. 5.

As a primer at the mutation site, there was used primer pE153 for obtaining the human CNTF mutant in which the glutamic acid residue at position 153 corresponding to the amino acid sequence of wild type human CNTF has been substituted with another amino acid residue (hereinafter the human CNTF mutant wherein the position 153 has been substituted is sometimes referred to as "E153 mutant"). In the corresponding sequence, the first and second codons were prepared as a mixture of G, A, T and C and the third codon as a mixture of G and C, at the synthesis stage. With respect to the objective site, all of the twenty amino acids are covered by these 32 primer mixtures.

Where the glutamine residue at position 63 is substituted with arginine residues pQ63R shown in FIG. 5 was employed as a single primer for the desired mutation. The procedures and conditions for constructing the mutant are the same as those described above, except for using pQ63R instead of pE153 as a primer for the mutation site. The human CNTF mutant in which glutamine residue at position 63 has been substituted with arginine residue may be sometimes referred to as "Q63R mutant".

Specifically, a first PCR was carried out using two primers, i.e., primer 1 at the 5' or 3' end of the structural gene and primer 2 (pE153 or pQ63R) at the mutation site. As primer 1, there was employed a primer #N described in FIG. 5, proximal to the mutation site. After amplification, electrophoresis was performed on agarose gel and the objective gene was cut out and purified. Utilizing the product and #C(RV) described in FIG. 5 as primers, the second PCR was conducted to amplify the full-length structural gene of human CNTF. At this stage, the product obtained by the first PCR was employed as a primer. The amplification could be made only in such a relatively narrow range of concentration as in the amount of approximately 1 to 2 pmols. The gene could not be amplified when the amount of the product produced by the first PCR was either too small or too large. An appropriate temperature for annealing was about 60° C. As a template, linear DNA obtained by digestion of pKKCNTF with PvuII was employed.

3) Preparation of an expression vector for the human CNTF mutant

After wild type human CNTF expression vector pKKCNTF was digested with BamHI and PstI and the wild type human CNTF structural gene sequence corresponding to a passenger was removed, the pKKCNTF was used as a vector. In this passenger (human CNTF mutant structural gene) segment to be integrated into this vector, the digestion site with BamHI and PstI is present also in the structural gene. For this reason, the BamHI and PstI site cannot be used. Therefore, the BglII (5' end) and EcoT22I (3' end) digestion sites which produce cohesive segments to these sites, respectively, are designed to locate in the primers for gene amplifications as shown in FIG. 5. After digestion with these restriction enzymes, the above digestion sites were integrated into the BamHI and PstI sites of the vector. That is, pKKCNTF was first digested with BamHI and PstI, and the desired gene was purified after electrophoresis, and then subjected to BAP treatment. On the other hand, the passenger prepared by gene amplification was digested with BglII and EcoT22I. Then ligation was performed using the thus prepared passenger (about 100 ng, about 10 times that of the vector in mole number) and the vector (about 100 ng) prepared above. The ligation product was transfected to strain JM109 in a manner as described below. With regard to the clone obtained, its nucleotide sequence was determined to identify the mutation. For determination of the nucleotide sequence, Sequenase DNA Sequence Kit (Toyobo Co., Ltd.) was used. The E153 mutant expression vector and the Q63R mutant expression vector were thus obtained.

Figure 6:
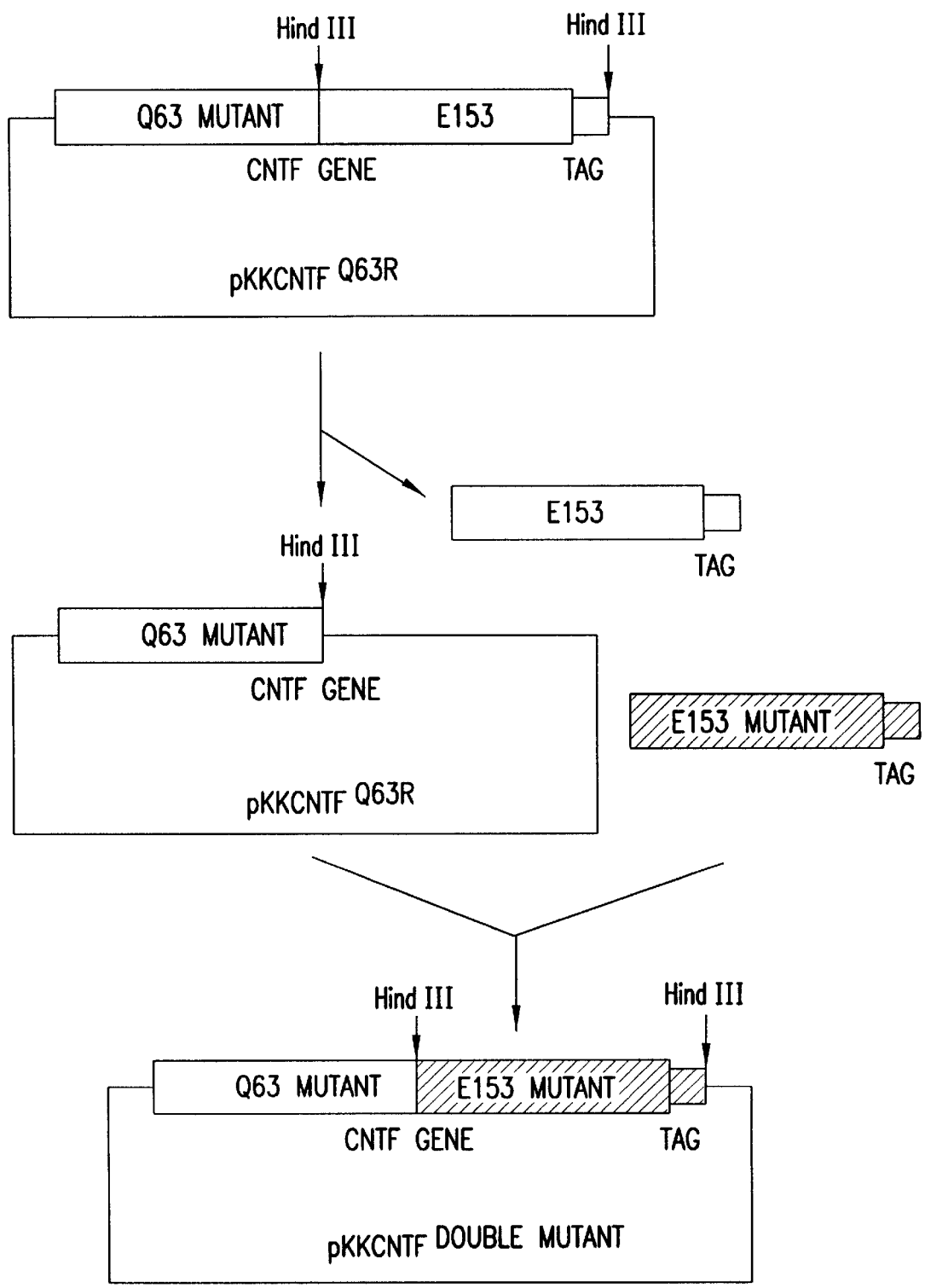
FIG. 6 shows an outlined method for constructing an expression vector for the human CNTF double mutant of the present invention which involves double substitutions at positions 153 and 63.

4) Preparation of the mutant gene in which double substitutions have occurred at positions 153/63 and an expression vector therefor As observed with pKKCNTF, the Q63R mutant expression rector contains two digestion sites with restriction enzyme HindIII, which are shown in FIG. 6 The passenger gene shown in FIG. 6 was replaced by the corresponding sequence of the E153 mutant gene to construct an expression vector for the mutant CNTF with double substitutions at positions 153 and 63. More specifically, the expression vector of the Q63R mutant obtained above was digested with HindIII followed by ligation to prepare the gene deleted of the passenger gene as shown in FIG. 60 The gene was further digested with HindIII. The digested DNA was purified and then treated with BAP, which was made a vector segment. On the other hands after each expression vector of the E153 mutant was digested with HindIII, the passenger segment of about 400 bp was isolated and purified followed by ligation using the vector segment prepared above, which was then likewise transfected to *E. coli* JM109 as later described. The clones obtained were examined if the passenger segment was integrated and as to the direction of the integration. The clones integrated with the passenger segment as intended were screened and reconfirmed for the mutation by determining the respective nucleotide sequences.

Table 1 shows 47 human CNTF mutants constructed by the above procedures.

TABLE 1

| Human CNTF mutants obtained in the present invention | | |
|---|---|---|
| Site of Mutation | Amino Acid After Substitution | Number of Kind |
| F152 | R | 1 |
| E153 | G, A, V, L, I, P, M, N, Q, D, H, K, R, F, Y, W | 16 |
| K154 | G, L, M, R | 4 |
| K155 | G, A, T, M, D, E, R | 7 |
| L156 | G, A, C, P, Q, D, E, H, K, R, F, W | 12 |
| W157 | G, L, S, C, P, E, K | 7 |

Representative examples of 20 types of the human NTF mutant expression vectors carrying mutations are shown below.

a) A vector capable of expressing the human CNTF mutant E153R of the present invention in which the position 153 has been mutated to arginine b) A vector capable of expressing the human CNTF mutant E153Y of the present invention in which the position 153 has been mutated to tyrosine c) A vector capable of expressing the human CNTF mutant E153F of the present invention in which the position 153 has been mutated to phenylalanine d) A vector capable of expressing the human CNTF mutant E153W of the present invention in which the position 153 has been mutated to tryptophane e) A vector capable of expressing the human CNTF mutant E153H of the present invention in which the position 153 has been mutated to histidine f) A vector capable of expressing the human CNTF mutant E153A of the present invention in which the position 153 has been mutated to alanine g) A vector capable of expressing the human CNTF mutant E153V of the present invention in which the position 153 has been mutated to valine h) A vector capable of expressing the human CNTF mutant E153L of the present invention in which the position 153 has been mutated to leucine i) A vector capable of expressing the human CNTF mutant E153I of the present invention in which the position 153 has been mutated to isoleucine j) A vector capable of expressing the human CNTF mutant E153H of the present invention in which the position 153 has been mutated to methionine k) A vector capable of expressing the human CNTF mutant E153Q of the present invention in which the position 153 has been mutated to glutamine l) A vector capable of expressing the human CNTF mutant E153N of the present invention in which the position 153 has been mutated to asparagine m) A vector capable of expressing the human CNTF mutant E153G of the present invention in which the position 153 has been mutated to glycine n) A vector capable of expressing the human CNTF mutant E153P of the present invention in which the position 153 has been mutated to proline o) A vector capable of expressing the human CNTF mutant E153K of the present invention in which the position 153 has been mutated to lysine p) A vector capable of expressing the human CNTF mutant E153D of the present invention in which the position 153 has been mutated to aspartic acid q) A vector capable of expressing the human CNTF mutant E153R/Q63R of the present invention in which the positions 153 and 63 have been both mutated to arginine r) A vector capable of expressing the human CNTF mutant E153Y/Q63R of the present invention in which the positions 153 and 63 have been mutated to tyrosine and arginine, respectively s) A vector capable of expressing the human CNTF mutant E153W/Q63R of the present invention in which the positions 153 and 63 have been mutated to tryptophane and arginine, respectively t) A vector capable of expressing the human CNTF mutant Q63R of the present invention in which the position 63 has been mutated to arginine 5) Preparation of *E. coli* transfected with the expression vector Approximately 100 ng of the wild type or mutant human CNTF-expressing vector DNA prepared above was mixed with 100 μl of JM109 competent cells commercially available (Toyobo Co., Ltd.). The mixture was allowed to stand in ice for 30 minutes. After heating at 42° C. for 30 seconds, the mixture was added to 900 μl of SOC medium (20 g of trypton, 5 g of yeast extract, 0.585 g of sodium chloride, 0.186 g of potassium chloride, 10 mM magnesium chloride, 10 mM magnesium sulfate and 20 mM glucose, per liter) followed by shake culture at 37° C. for about an hour. The medium was spread over LB agar medium (10 g of trypton, 5 g of yeast extract, 5 g of sodium chloride and 15 g of agar (pH 7), per liter) containing 50 μg/ml of ampicillin. The *E. coli* transformants were screened.

EXAMPLE 2

1) Expression of the human CNTF mutant in *E. coli*

After the transfection of *E. coli* using the human CNTF mutant expression vector of the present invention obtained in Example 1, the human CNTF mutant was expressed utilizing the *E. coli* transformant. For the expressions minimum culture was performed in TYGPN medium (20 g of trypton, 10 g of yeast extracts 8 ml of glycerine, 5 g of sodium primary phosphate, and 1 g of potassium nitrate (pH 6.1), per liter).

That is, 100 μl of seed culture of the *E. coli* JM109 transformant was added to 900 μl of TYGPN medium supplemented with 50 μg/ml of ampicillin and shake culture was then conducted at 37° C. Two hours later, IPTG was added to the medium in a final concentration of 1 mM. Incubation was continued for 3 hours. After centrifugation, the following lysis procedures were carried out. To the medium pellet was added 100 μl of lysis solution (50 mM Tris-HCl (pH 8.0), 1 m EDTA, 100 mM NaCl, 0.27 mg/ml lysozyme, 0.13 mM PMSF and 60 U DNaseI). After digestion at 37° C. for an hour, the lysate was centrifuged at 15000 rpm for 15 minutes. The supernatant of the lysate was used as a sample for concentration assay by SDS-PAGE and for determining the survival promoting activity on DRG neurons. For determination of the survival promoting activity on DRG neurons, 50 µl of the lysate supernatant was diluted in 950 µl of PBS containing 0.1% BSA and the dilution was filtered to remove bacteria, which was used as a sample.

2) Confirmation of expression of the human CNTF mutant by SDS-PAGE and quantitative determination of the mutant SDS-PAGE was performed under the following conditions.

Commercially available 15%–25% polyacrylamide concentration gradient gel (DAI-ICHI KAGAKU YAKUHIN Co., Ltd.) was employed. From the lysate supernatant 4 µl was taken and placed on each well. Electrophoresis was performed at a constant current of 40 mA for an hour.

Figure 7A:
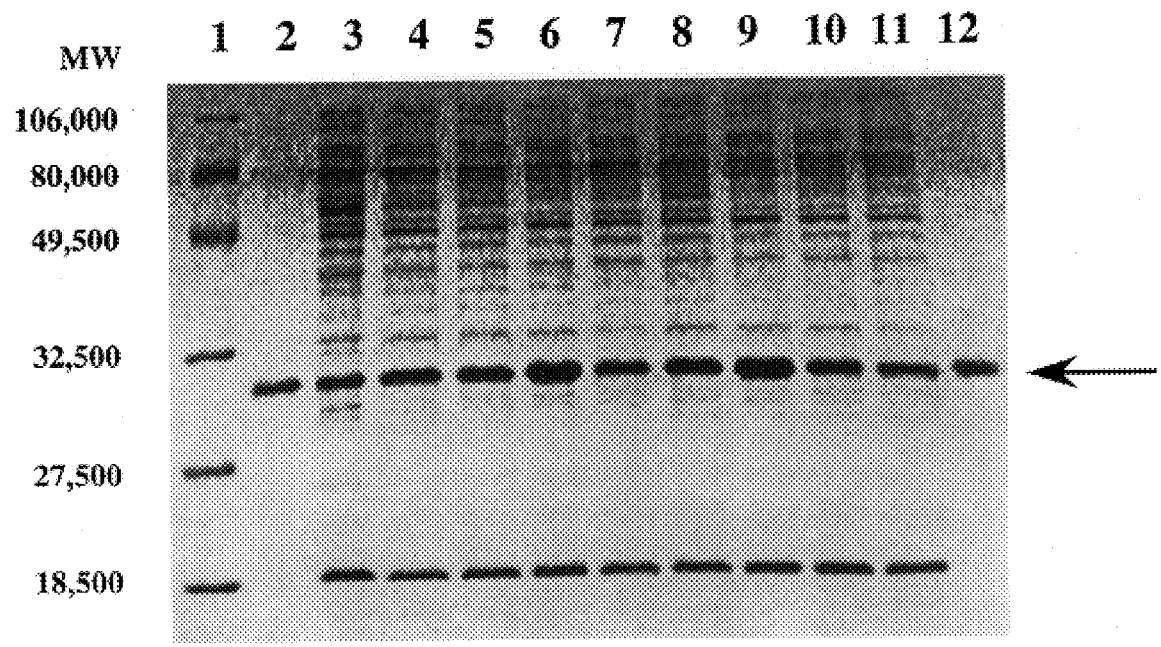
FIG. 7(A)
Figure 7B:
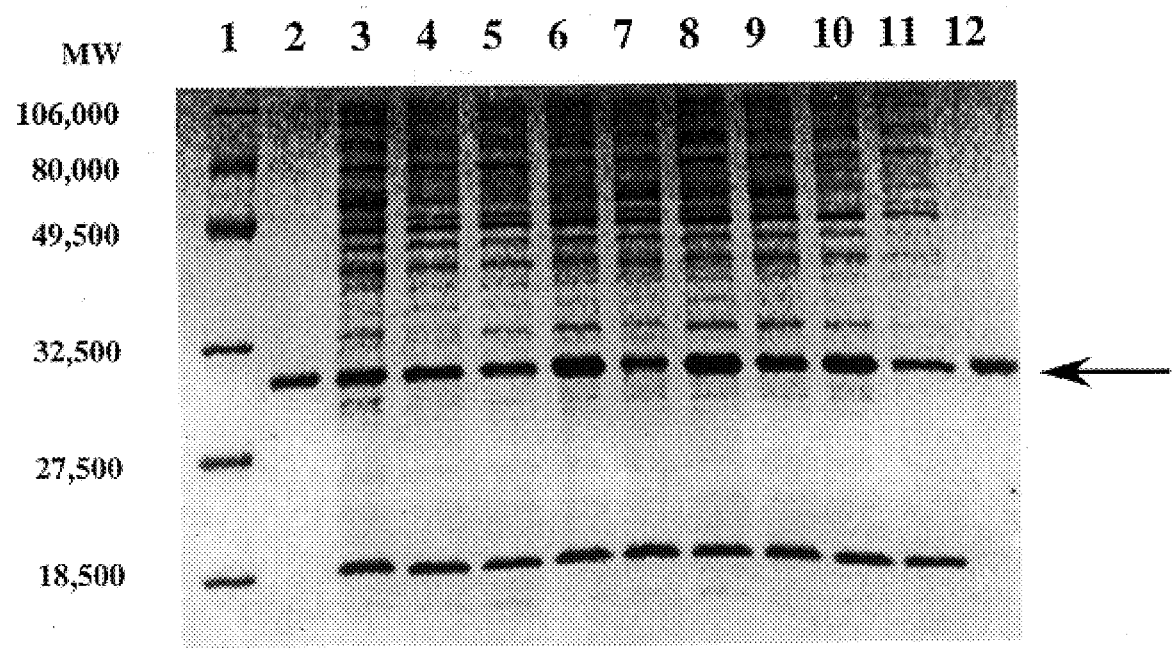
FIG. 7 indicates photographs showing the results of electrophoresis of the human CNTF mutants of the present invention by SDS-PAGE. The lanes shown in FIG. 7 denote the electrophoretic patterns of the following.

The electrophoretic patterns of the E153 mutants obtained by SDS-PAGE are shown in FIG. 7(A) and (B). The lanes in FIGS. 7(A) and (B) denote the electrophoretic patterns of the followings

FIG. 7(A)

Lane 1: markers of the indicated molecular weight

Lanes 2 and 12: purified wild type human CNTF expressed in *E. coli*

Lane 3: the aforesaid lysate supernatant of wild type human CNTF

Lanes 4–11: the aforesaid lysate supernatant of the E153 mutants (4: 153R, 5: E153K, 6: E153A, 7: E153V, 8: E153L, 9: E153G, 10: E153P and 11: E153I) obtained in this Example

FIG. 7(B)

Lane 1: markers of the indicated molecular weight

Lanes 2 and 12: purified wild type human CNTF expressed in *E. coli*

Lane 3: the aforesaid lysate supernatant of wild type human CNTF

Lanes 4–11: the aforesaid lysate supernatants of the E153 mutants (4: 153Y, 5: E153F, 6: E153W, 7: E153H, 8: E153M, 9: E153Q, 10: E153N and 11: E153D) obtained in this Example The position of human CNTP is shown by arrow. The mobility of the E153 mutant is identical with that of wild CNTF.

The electrophoretic patterns of the E153 mutants, the Q63 mutants and the E153/Q63 double mutants having the two mutations of the invention were obtained by SDS-PAGE and are shown in FIG. 8. The lanes in FIG. 8 denote the electrophoretic patterns of the following:

Lane 1: purified wild type human CNTF expressed in *E. coli*

Lane 2: the aforesaid lysate supernatant of wild type human CNTF

Lanes 3–9: the aforesaid lysate supernatants of the mutants (3: Q63R, 4: E153R, 5: E153Y, 6: E153W, 7: E153R/Q63R; 8: E153Y/Q63R and 9: E153W/Q63R) obtained in this Example The mobilities of wild type human CNTF and Q63R mutant are shown by—(1) and—(2), respectively.

The images of the electrophoretic results were scanned with a scanner and the concentration of the gel band derived from CNTF was quantitatively determined using an image processing software (NIH Image 1.47). For example, the concentrations of wild type human CNTF and the human CNTF mutant E153R were quantitatively determined to be 6.4 µg/ml and 7.0 µg/ml, respectively.

3) Quantitative determination of the human CNTF mutant by ELISA

Utilizing purified anti-wild type human CNTF antibody, the concentration of the human CNTF mutant in a sample was assayed by sandwich ELISA. That is, 50 µl of a sample to be assayed was placed on a 96-well plate to which anti-wild type human CNTF antibody had been immobilized, which was then allowed to stand at 4° C. overnight. Each well was rinsed 3 times with 200 µl each of PBS and reacted with 50 µl of biotinated anti-wild type human CNTF antibody (diluted by 1000-fold in 3% BSA/PBS/NaN$_3$). After rinsing 3 times with 200 µl each of PBS, 50 µl of alkaline phosphatase-bound streptoavidin (diluted by 2000-fold in 3% BSA/PBS/NaN$_3$) (VEC Inc.) was added to each well and allowed to stand at room temperature for 2 hours. After rinsing again 3 times with 200 µl each of PBS, 0.05 mg/ml PNPP-containing solution buffered with 0.1M sodium carbonate and 1 mM magnesium chloride (pH 9.8) was added for measurement at 415 nm. The purified anti-wild type human CNTF antibody used above was prepared by affinity chromatography using wild type human CNTF as a ligand.

Wild type human CNTF and the human CNTF mutant E153R were determined to have concentrations of 7.6 µg/ml and 7.9 µg/ml, respectively. The concentrations thus determined almost coincided with those deduced from the results of SDS-PAGE. With respect to the other mutants, the data quantitatively determined by SDS-PAGE were almost in agreement with those obtained by ELISA. The concentrations obtained by SDS-PAGE are shown in FIGS. 9 through 15.

EXAMPLE 3

Assay of the human CNTF mutants of the invention for the activity

The activity of each human CNTF mutant obtained in Example 2 was assayed by measuring the survival promoting activity on chicken dorsal root ganglion (DRG) neurons. That is, DRG neurons were prepared from 10-day-old chicken embryo (E10). After treating with 0.125% trypsin and DNaseI, the DRG neurons were preincubated in 5% FCS-supplemented DMEM medium at 37° C. for 30 minutes. The DRG neurons were collected, dissociated and then incubated in 5% FCS-supplemented DMEM medium using a 96-well plate coated with 0.5 mg/ml of polyornithine (100 µl aliquot in each wells 37° C. 72 hours). The cells surviving after the incubation was assayed in terms of the reductivity when 10 µg of MTT was added and the amount of the formazan formed was determined by measuring the absorbance at 570 nm. After the preincubation, the final concentration of each CNTF mutant was adjusted in a range of 0.001 ng/ml to 100 ng/ml.

For controls, wild type human CNTF was used to determine the survival promoting activity on DRG neurons. The wild type human CNTF and the respective human CNTF mutant samples were prepared by the same method at the same time.

With respect to the mutants E153R, E153Y, E153H, E153F and E153W in which the 153 glutamic acid residue has been substituted with arginine residue, tyrosine residue, histidine residue, phenylalanine residue and tryptophane residue, respectively, the survival promoting activity on chicken ciliary ganglion (CG) neurons was also examined as follows. That is, CG neurons were excised out of 8-day-old chicken embryo (E8). After treating with 0.125% trypsin and DNaseI, the CG neurons were preincubated in 5% FCS-supplemented DMEM medium at 37° C. for 60 minutes. The CG neurons were collected, dissociated and then incubated in 5% FCS-supplemented DMEM medium using a 96-well plate coated doubly with 0.5 mg/ml of polyornithine and 5 µg/ml of laminine (100 µl aliquot in each wells 37° C., 24 hours). Regarding the surviving cells after the incubation, the absorbance was measured to evaluate the survival promoting activity using MTT, as in the case of DRG.

As a part of the results for evaluating the survival promoting activity in this Example, the following human CNTF mutants were examined and the results are shown in FIGS. 9 through 15, in comparison with human CNTF for control. That is, FIG. 9 shows the survival promoting activity of the recombinant wild type human CNTF in the supernatant dilutions of the lysates prepared as described above and purified wild type human CNTF on chicken DRG neurons; FIGS. 10 through 13 show the survival promoting activity of the E153 mutants on chicken DRG neurons; FIG. 14 shows the survival promoting activity of the mutants E153R, E153Y, E153H, E153F and E153W on chicken CG neurons; and FIG. 15 shows the survival promoting activity of the mutants E153R, E153Y, E153H, E153F and E153W on rat DRG neurons. In FIGS. 9 through 15, the ordinate represents an absorbance at 570 nm (showing the formation of formazan) and the abscissa represents a concentration of the CNTF added.

The survival promoting activity of recombinant wild type human CNTF and the single mutants occurred at either position E153 or position Q63 and the double mutants occurred at both positions E153 and Q63 on chicken DRG neurons was also assayed. The results are shown in FIG. 16. FIG. 16 shows the activity assayed when wild type human CNTF and each human CNTF mutant were applied to chicken DRG neurons, respectively, in a final concentration of 1 ng/ml, wherein the ordinate represents a survival rate (%) of CNTF responsive cell expressed by a percentage of absorbance of the formed formazan at 570 nm, when the absorbance of formazan formed by applying 100 ng/ml of CNTF or the CNTF mutant is made 100% (in this experiments $A_{570}=0.19$ is made 100%). In FIG. 16, "PBS" and "Wild" mean the results of blank tests obtained by adding a 0.1% BSA-containing PBS solution and wild type human CNTF, respectively, in place of the CNTF mutant.

1) Activity of recombinant natural human CNTF in the lysate supernatant dilution FIG. 9 shows a comparison between the recombinant wild type human CNTF in the lysate supernatant dilution and the purified wild type human CNTF in the survival promoting activity on chicken DRG neurons. Since the two CNTFs displayed almost the same activity, it was confirmed quantitatively that the recombinant wild type human CNTF in the lysate supernatant was in an active form.

2) Activity of the E153 mutants on chicken DRG neurons

As noted from FIGS. 10 to 13, the mutants in which the amino acid residue at position 153 has been substituted with a residue of methionine, leucine, valine, alanine, glutamine, asparagine, glycine, proline and lysine residues, respectively (the mutants E153M, E153L, E153V, E153A, E153Q, E153N, E153G, E153P and E153K) exhibited the survival promoting activity higher by 2 to 3 times than that of wild type human CNTF in which the position 153 is glutamic acid. Where the amino acid residue at position 153 has been substituted with arginine, histidine, tyrosine, phenylalanine and tryptophane residues, respectively (the mutants E153R, E153H, E153Y, E153F and F153W), the mutants showed the survival promoting activity higher than about 10 times than that of wild type human CNTF. Further where the amino acid residue at position 153 has been substituted with aspartic acid or isoleucine (the mutants E153D, E153I), these mutants displayed the survival promoting activity comparable to that of wild type type.

The E153 mutants and the Q63R mutants with single mutation at position 153 or 63 displayed the survival promoting activity higher than that of wild type human CNTF. It has been confirmed that these single mutants had almost the same specific activity. The double mutants in which mutations occurred at positions 153 and 63 displayed the specific activity higher than the respective single mutants (FIG. 16).

Based on the foregoing results, the mutants having a very higher or higher specific activity than that of wild type human CNTF are summarized in Table 2 below.

TABLE 2

| | Substitution of Amino Acid | |
|---|---|---|
| Substituted Position | Mutant having a very higher specific activity than that of wild type CNTF | Mutant having a higher specific activity than that of wild type CNTF |
| Position 153 (Glu) | Arg, His, Try, Phe, Trp | Met, Leu, Val, Ala, Gln, Asn, Gly, Pro, Lys |

The foregoing results reveal and suggest the follows.

It is considered that negative charges at position 153 would be disadvantageous for expressing the activity of human CNTF, since the activity is low when the position 153 is glutamic acid wild type human CNTF) or aspartic acid. This is supported by the fact that the activity increased by the mutation without negative charges. The reason that the E153R mutant displayed a very higher activity is considered to be because arginine having charges opposite to those of glutamic acid has been introduced at position 153 in this mutant.

Furthermore, where the aromatic amino acid was introduced into the position 153 as in the mutants E153Y, E153F, E153W and E153H, the survival promoting activity was extremely higher, suggesting a hydrophobic interaction with the receptor or some interaction with other residue(s) inside CNTF which is beneficial for the activity.

In the mutations at positions E153 and Q63 which were identified to be effective for enhancing the specific activity, the combination of the mutations at the two positions was shown to increase the activity to the sum of the respective mutations. These two sites are located at three-dimensionally different positions as shown in FIG. 17. It is thus considered that where the mutation is generated at the two positions in one molecules the effect of the double mutant would be produced as the sum of the two mutations at the respective positions.

3) Activity of the E153 mutants on chicken CG neurons

As shown in FIG. 14D the mutants E153R, E153H, E153Y, E153F and E153W in which the 153 amino acid residue has been substituted with arginine residue, histidine residues tyrosine residue, phenylalanine residue and tryptophane residue, respectively, exhibited the survival promoting activity higher by almost 10 times than that of wild type human CNTF with glutamic acid at position 153.

The mutants having a high specific activity on DRG neurons showed a survival promoting activity also on CG neurons higher than that of wild type human CNTF, which suggests that these mutants would also exhibit a survival promoting activity on other types of neuron higher than that of wild type human CNTF.

4) Activity of the E153 mutants on rat DRG neurons

As shown in FIG. 15, the mutants E153R, E153H, E153Y, E153F and E153W in which the 153 amino acid residue has been substituted with arginine residues histidine residue, tyrosine residues phenylalanine residue and tryptophane residues respectively, exhibited the survival promoting activity higher by almost 10 times than that of wild type human CNTF with glutamic acid at position 153.

The results suggest that the mutants having a high specific activity on neurons from the chicken which is the Aves would give a higher survival promoting activity also on the neurons of rat which is a mammalian. The results further suggests that these mutants would also exhibit a survival promoting activity on human neurons higher than that of wild type human CNTF.

The survival promoting activity of the K155 single mutants on chicken DRG neurons was further assayed under similar conditions. The results are shown in FIG. 18.

5) Activity of the K155 mutants on chicken DRG neurons

FIG. 18 indicates the survival promoting activity of the mutants K155R, K155A and K155H on chicken DRG neurons. The activity less than 1% of wild type CNTF was maintained only in the case of substitution with arginine residue having positive charges as the original lysine residue has. However, the activity was lost in the case of substitution with the other amino acid residue.

6) Activity of the D1 cap region-mutated mutants on chicken DRG neurons

The survival promoting activity of the mutants obtained in this Example, which have been mutated in the D1 cap region of human CNTF, is shown in FIG. 19. The activity of the mutants with mutation other than the positions 153 and 155 described above was also greatly varied depending upon the site of mutation.

Where the 155 amino acid has been replaced, the role of the original lysine at position 155 cannot be compensated for either by methionine residue having almost the same length as that of the lysine residue or by alanine residue having a shorter length and thus considered to be free from steric hindrance. This fact suggests that the lysine residue at position 155 would be strictly recognized by the receptor of CNTF. Furthermore, though not shown as a working examples purified K155A mutant protein shows almost the same helically polarized dichroic (CD) spectrum as that of purified wild type human CNTF protein. It is therefore considered that the mutant K155A which has lost its activity would keep almost the same conformation in the whole as that of wild type human CNTF. Since the mutant K155A inhibits the binding between wild type human CNTF and the receptor, it is considered that the activity-lost K155A mutant would maintain the binding ability to the CNTF receptor. From the foregoing it is predicted that the lysine residue at position 155 would be essential for the signal transduction into cells.

The role of the other amino acid residues in the D1 cap region is yet unclear, unlike the amino acids at positions 153 and 155 described above. However, it is predicted that at least the amino acid residues at positions 156 and 157 would be important and responsible for the activity attributed to the D1 cap regions In any event, it is considered that the activity would not be attributable to only one residue but an active structure as a whole would be formed by the D1 cap region composed of the residues around the position 155, which region would be strictly recognized by the CNTF receptor. Therefore, the D1 cap region as a whole is considered important for the activity.

Assuming that the human CNTF mutant of the present invention would be structurally homologous to human growth hormone (hGH), the mutation segments are placed on the three-dimensional structure of hGH, which are indicated in FIG. 17 as "E153" in D1 cap region and "Q63". The numerals in FIG. 17 denote the numbering of the corresponding amino acid residue in wild type human CNTF.

EXAMPLE 4

Prediction of the amino acid sequence (residue) effective for the mutation in a CNTF-homologous protein 1) Comparison with a CNTF-homologous protein in amino acid sequence As described above, it is reported by Bazan that in the α-helix-abundant cytokines which are structurally homologous to CNTF proteins, the sequence called D1 motif similar to an amino acid sequence is present in the D1 cap region (J. F. Bazan, Neuron, 7, 197 (1991). The role of each amino acid has been clarified for the first time in the present invention. The amino acid sequence which is predicted to be the D1 cap region in each protein is shown in Table 3. In Table 3, the proteins are classified into the long chain group and the short chain group and in the long chain group, the proteins are classified into the subgroup utilizing gp130 as the receptor (CNTF belongs to this group) and the subgroup utilizing other receptor types.

TABLE 3

Amino Acid sequences of 4-helix bundle structure proteins in the D1 cap region

| Sub-Group Protein | φ | F/W | E/Q | K/R | K/R | K/φ | X | G | Number of Amino Acid Residues | Sequence Identifier (SEQ ID NO: 12) |
|---|---|---|---|---|---|---|---|---|---|---|
| human CNTF† | L | F | E | K | K | L | W | G | 151–158 | (SEQ ID NO: 13) |
| rat CNTF† | L | F | E | K | K | L | M | G | 150–157 | (SEQ ID NO: 14) |
| rabbit CNTF† | L | F | E | K | K | L | W | G | 151–158 | (SEQ ID NO: 15) |
| human LIF* | V | F | Q | K | K | K | L | G | 154–161 | (SEQ ID NO: 16) |
| mouse LIF* | A | F | Q | R | K | K | L | G | 154–161 | (SEQ ID NO: 17) |
| human OSM* | A | F | Q | R | K | L | E | G | 159–166 | (SEQ ID NO: 18) |
| simian OSM† | V | F | Q | R | K | L | E | G | 159–166 | (SEQ ID NO: 19) |
| human IL-6* | Q | W | L | Q | D | M | T | T | 157–164 | (SEQ ID NO: 20) |
| mouse IL-6* | E | W | L | R | T | K | T | I | 157–164 | (SEQ ID NO: 21) |
| human IL-11† | G | G | I | R | A | A | H | A | 148–155 | (SEQ ID NO: 22) |
| monkey IL-11† | G | G | I | R | A | A | H | A | 148–155 | (SEQ ID NO: 23) |
| human G-CSF* | A | F | Q | R | R | A | G | G | 143–150 | (SEQ ID NO: 24) |

TABLE 3-continued

Amino Acid sequences of 4-helix bundle structure proteins in the D1 cap region

| Sub-Group Protein | φ | F/W | E/Q | K/R | K/R | K/φ | X | G | Number of Amino Acid Residues | Sequence Identifier (SEQ ID NO: 12) |
|---|---|---|---|---|---|---|---|---|---|---|
| mouse G-CSF* | A | F | Q | R | R | A | G | G | 144–151 | (SEQ ID NO: 25) |
| chicken MGF† | P | F | Q | Q | Q | V | G | G | 147–154 | (SEQ ID NO: 26) |
| human GH* | S | H | N | D | D | A | L | L | 150–157 | (SEQ ID NO: 27) |
| human PRL† | M | A | D | E | E | S | R | L | 158–165 | (SEQ ID NO: 28) |
| human EPO† | D | T | F | R | K | L | F | R | 136–143 | (SEQ ID NO: 29) |
| human IFN$_\alpha$* | L | T | E | K | K | Y | S | P | 131–138 | (SEQ ID NO: 30) |
| human IL-2† | E | F | L | N | R | W | I | T | 116–123 | (SEQ ID NO: 31) |
| human IL-3* | E | F | R | R | K | L | T | F | 106–113 | (SEQ ID NO: 32) |
| human IL-4† | T | L | E | N | F | L | E | R | 112–119 | (SEQ ID NO: 33) |
| human IL-5† | G | E | E | R | R | R | V | N | 106–113 | (SEQ ID NO: 34) |
| human GM-CSF† | T | F | E | S | F | K | E | N | 102–109 | (SEQ ID NO: 35) |

In Table 3 above, the 4-helix bundle structure proteins were classified into the following three subgroups. That is, the proteins in the long chain subgroup which interact with gp130 (IA), the proteins in the long chain subgroup which do not interact with gp130 (IB), and the proteins in the short chain subgroup (II). Amino acids are expressed by one letter code. In Table 3, the following symbols denote:

φ: a hydrophobic amino acid
X: any amino acid residue
*: Bazan's prediction (J. F. Bazan, Neuron, 7, 197 (1991))
†: Inventors' prediction The abbreviations used in Table 3 denote:
LIF: leukocyte inhibitory factor
OSM: oncostatin H
G-CSF: granulocyte colony-stimulating factor
MGF: myelomonocyte growth factor
GH: growth hormone
PRL: prolactin
EPO: erythropoietin
IFNα: interferon α
GM-CSF: granulocyte macrophage colony-stimulating factor As in the case of human CNTF, the protein having a sequence similar to D1 motif is observed abundantly in the long chain protein group. Such a protein showed high sequence similarity to LIF and OSM which utilize gp130 as the receptor and to G-CSF.

2) Application of the results on known structure-activity relationship analysis on a CNTF-homologous protein With regard to cytokines abundant in α-helices, many analyses have been made on the structure-analysis relationship to date. The results of such structure-activity relationship analyses on the proteins, which belong to the long chain group having higher sequence similarity to human CNTF protein, are briefly summarized in FIG. 20. The proteins are classified and indicated into two subgroups, one utilizing gp130 as the receptor and another using other receptors. The regions empirically proved to be important for the activity expression are shown by dotted areas and the regions predicted to be associated with the activity expression are shown by the areas formed by dashed lines.

With respect to the boundary region between the CD loop and helix D including D1 cap regions the importance for receptor binding is reported on IL-6 (J. P. J. Brakenhoff et al., J. B. C., 269, 86 (1994)) and on LIF (R. C. Robinson et al., Cell, 77, 1101 (1994)), as described hereinabove (however, the amino acid sequence in the D1 cap region of IL-6 has no similarity to D1 motif and therefore, it is impossible to identify the important amino acid residues on D1 motif; the amino acid sequence of LIF in the same region has high similarity to D1 motif but any important amino acid residue has not been identified). With respect to the α-helical cytokines, no report has been made to show that the D1 region will be important for the activity; an exception is G-CSF which will be described hereinafter In the present invention, the D1 cap region has been established to be important in human CNTF. Accordingly, it is considered to utilize gp130 as the receptor, as a consensus sequence of the protein utilizing the D1 cap region for receptor binding. As the proteins belonging to this subgroup, there are known LIF, OSM, IL-6 and IL-11, in addition to CNTF. It is highly likely that in these proteins, the amino acid residues corresponding to the D1 cap region would be associated with receptor binding for the activity expression.

In particulars LIF and OSM have high sequence similarity to D1 motif. It is therefore predicted that the same effect as brought by the mutation in the D1 cap region in human CNTF would result in each protein by the mutation at the corresponding site. More specifically, it is predicted that the activity would be seriously reduced by the mutation at position 158 of LIF and position 163 of OSM, which correspond to the 155 lysine residue in human CNTF. It is also predicted that the activity would be increased by the mutation at position 156 of LIF and position 161 of OSM, which correspond to the 153 glutamic acid residue in human CNTF. It is further predicted that the mutation of not only the two amino acid residues but other residues in the D1 motif would affect their biological activity Among the proteins that do not utilize gp130 or there is no report to utilize gp130, G-CSF is known to be extremely similar to the sequence of D1 motif. For G-CSF, there is a report that a monoclonal antibody capable of recognizing the region around the D1 motif neutralizes the activity of G-CSF. (J. E. Layton et al., J. B. C., 266, 23815 (1991)), suggesting that the D1 cap region will take part in receptor binding. That is, it is predicted that the activity would increase, as in the case of human CNTF, by the mutation of the 146 glutamic acid residue in G-CSF, which corresponds to the 153 glutamic acid residue in human CNTF. It is therefore predicted that a change in the activity would occur by varying the other amino acid(s) in the D1 motif. It is further predicted that the same would apply to a myelomonocyte growth factor (MGF) which has been reported to be similar in sequence to G-CSF, suggesting that the activity would change or increase by the mutation in the D1 cap region of MGF. Receptor binding in the consensus sequence of the D1 motif may be generally observed in proteins, in addition to the proteins utilizing gp130 as their receptor.

Industrial Applicability

The human CNTF mutants of the present invention display the activity comparable or superior to that of wild type human CNTF. It is therefore expected that the human CNTF mutants would be effective for medicaments with improved side effects such as reduction in appearance of an autoantibody, loss of body weight, anorexia, a dry cough, fatigue, etc.

The mutants protein that are predictable in the present invention will also display the activity comparable or superior to that of the corresponding wild type proteins. It is therefore expected that these predictable mutants protein would be also effective as medicaments with reduced side effects such as reduction in appearance of an autoantibody and other side effects. It is also expected that as an absolute dose is reduced, any harmful contaminants in these wild type proteins will be eliminated or decreased and production scale will be reduced.

We claim:

1. A mutant human ciliary neurotrophic factor (CNTF), wherein at least glutamic acid at a position corresponding to position 153 of wild type human CNTF having the amino acid sequence of SEQ ID NO:1 is substituted with another amino acid.

2. The mutant of claim 1, wherein said amino acid at said position corresponding to position 153 is tyrosine, phenylalanine, tryptophan, histidine or arginine.

3. The mutant of claim 1, further comprising substitution of glutamine at a position corresponding to position 63 of said wild type human CNTF with another amino acid.

4. A mutant human ciliary neurotrophic factor (CNTF), wherein at least lysine at a position corresponding to position 155 of wild type human CNTF having the amino acid sequence of SEQ ID NO:1 is substituted with another amino acid.

5. A mutant human ciliary neurotrophic factor (CNTF), wherein at least one amino acid of a D1 cap region in wild type human CNTF is substituted with an amino acid not found at that region of said wild type CNTF, wherein said D1 cap region is located at positions corresponding to positions 151–158 of said wild type human CNTF and comprises:

-Leu-Phe-Glu-Lys-Lys-Leu-Trp-Gly- (SEQ ID NO:13).

6. A mutant human leukemia inhibitory factor (LIF), wherein at least one amino acid of a D1 cap region in wild type human LIF is substituted with an amino acid not found at that region of said wild type human LIF, wherein said D1 cap region is located at positions corresponding to positions 155–162 of said wild type human LIF and comprises:

-Val-Phe-Gln-Lys-Lys-Lys-Leu-Gly- (SEQ ID NO:16).

7. A mutant human oncostatin M (OSM), wherein at least one amino acid of a D1 cap region in wild type human OSM is substituted with an amino acid not found at that region of said wild type human OSM, wherein said D1 cap region is located at positions corresponding to positions 159–166 of said wild type human OSM and comprises:

Ala-Phe-Gln-Arg-Lys-Leu-Glu-Gly- (SEQ ID NO:18).

8. A mutant human granulocyte colony stimulating factor (G-CSF), wherein at least one amino acid of a D1 cap region in wild type human is substituted with an amino acid not found at that region of said wild type human G-CSF, wherein said D1 cap region is located at positions corresponding to positions 143–150 of said wild type human G-CSF and comprises:

-Ala-Phe-Gln-Arg-Arg-Ala-Gly-Gly- (SEQ ID NO:24).

\* \* \* \* \*

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
        (A) LENGTH: 200 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:1:

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Tyr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Thr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Gln Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195                 200
```

(2) INFORMATION FOR SEQ ID NO:2:

(i) SEQUENCE CHARACTERISTICS:

```
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GAATTCCCGG GGATCCGTCG ACCTGCAGCC AAGCTT                                    36

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:3:

CGGAGATCTT TTTTTATAAA ATCAGGAGG                                            29

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:4:

CAAGCTTGGA TGCATGTCAG AGAAGGGAC                                            29

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:5:

GTGGTCTCNN NGAGAAGAAG CTG                                                  23

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:6:

GGTCTCTTTN NNAAGAAGCT GTG                                                  23

(2) INFORMATION FOR SEQ ID NO:7:

(i) SEQUENCE CHARACTERISTICS:
        (A) LENGTH: 20 base pairs
```

(B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO:7:

CTCTTTGAGN NNAAGCTGTG                                                       20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO:8:

CTTTGAGAAG NNNCTGTGGG                                                       20

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO:9:

GAGAAGAAGN NNTGGGGCCT AAAG                                                  24

(2) INFORMATION FOR SEQ ID NO:10:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO:10:

GAAGAAGCTG NNNGGCCTAA AG                                                    22

(2) INFORMATION FOR SEQ ID NO:11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO:11:

GCTCACTCCA ACGATCAGTG C                                                     21

(2) INFORMATION FOR SEQ ID NO:12:

(i) SEQUENCE CHARACTERISTICS:
            (A) LENGTH: 8 amino acids

```
          (B) TYPE: amino acid
          (C) STRANDEDNESS:
          (D) TOPOLOGY: linear (ii) MOLECULE TYPE: peptide (ix) FEATURE:
          (A) NAME/KEY: Peptide
          (B) LOCATION: 1..8
          (D) OTHER INFORMATION: Consensus (xi) SEQUENCE DESCRIPTION: SEQ ID NO:12:

Xaa Xaa Xaa Xaa Xaa Xaa Xaa Gly
1               5

(2) INFORMATION FOR SEQ ID NO:13:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:13:

Leu Phe Glu Lys Lys Leu Trp Gly
1               5

(2) INFORMATION FOR SEQ ID NO:14:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:14:

Leu Phe Glu Lys Lys Leu Met Gly
1               5

(2) INFORMATION FOR SEQ ID NO:15:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:15:

Leu Phe Glu Lys Lys Leu Trp Gly
1               5

(2) INFORMATION FOR SEQ ID NO:16:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:16:

Val Phe Gln Lys Lys Lys Leu Gly
1               5
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Ala Phe Gln Arg Lys Lys Leu Gly
1               5
```

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Ala Phe Gln Arg Lys Leu Glu Gly
1               5
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Val Phe Gln Arg Lys Leu Glu Gly
1               5
```

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

```
Gln Trp Leu Gln Asp Met Thr Thr
1               5
```

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

```
Glu Trp Leu Arg Thr Lys Thr Ile
1               5
```

(2) INFORMATION FOR SEQ ID NO:22:

(i) SEQUENCE CHARACTERISTICS:
       (A) LENGTH: 8 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:22:

Gly Gly Ile Arg Ala Ala His Ala
1               5

(2) INFORMATION FOR SEQ ID NO:23:

(i) SEQUENCE CHARACTERISTICS:
       (A) LENGTH: 8 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:23:

Gly Gly Ile Arg Ala Ala His Ala
1               5

(2) INFORMATION FOR SEQ ID NO:24:

(i) SEQUENCE CHARACTERISTICS:
       (A) LENGTH: 8 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:24:

Ala Phe Gln Arg Arg Ala Gly Gly
1               5

(2) INFORMATION FOR SEQ ID NO:25:

(i) SEQUENCE CHARACTERISTICS:
       (A) LENGTH: 8 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:25:

Ala Phe Gln Arg Arg Ala Gly Gly
1               5

(2) INFORMATION FOR SEQ ID NO:26:

(i) SEQUENCE CHARACTERISTICS:
       (A) LENGTH: 8 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:26:

Pro Phe Gln Gln Gln Val Gly Gly
1               5

(2) INFORMATION FOR SEQ ID NO:27:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

```
Ser His Asn Asp Asp Ala Leu Leu
1               5
```

(2) INFORMATION FOR SEQ ID NO:28:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

```
Met Ala Asp Glu Glu Ser Arg Leu
1               5
```

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

```
Asp Thr Phe Arg Lys Leu Phe Arg
1               5
```

(2) INFORMATION FOR SEQ ID NO:30:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Leu Thr Glu Lys Lys Tyr Ser Pro
1               5
```

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Glu Phe Leu Asn Arg Trp Ile Thr
1               5
```

(2) INFORMATION FOR SEQ ID NO:32:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Glu Phe Arg Arg Lys Leu Thr Phe
1               5
```

(2) INFORMATION FOR SEQ ID NO:33:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Thr Leu Glu Asn Phe Leu Glu Arg
1               5
```

(2) INFORMATION FOR SEQ ID NO:34:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
Gly Glu Glu Arg Arg Arg Val Asn
1               5
```

(2) INFORMATION FOR SEQ ID NO:35:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Thr Phe Glu Ser Phe Lys Glu Asn
1               5
```